US007872027B2

(12) United States Patent
Metallo et al.

(10) Patent No.: US 7,872,027 B2
(45) Date of Patent: Jan. 18, 2011

(54) LOW MOLECULAR WEIGHT MYC-MAX INHIBITORS

(75) Inventors: Steven J. Metallo, Silver Springs, MD (US); Edward V. Prochownik, Pittsburgh, PA (US)

(73) Assignees: University of Pittsburgh - Of the Commonwealth System of Higher Education, Pittsburgh, PA (US); Georgetown University, Washington, DC (US)

( * ) Notice: Subject to any disclaimer, the term of this patent is extended or adjusted under 35 U.S.C. 154(b) by 818 days.

(21) Appl. No.: 11/707,421

(22) Filed: Feb. 16, 2007

(65) Prior Publication Data
US 2007/0203188 A1 Aug. 30, 2007

Related U.S. Application Data

(60) Provisional application No. 60/774,501, filed on Feb. 17, 2006.

(51) Int. Cl.
*A61K 31/427* (2006.01)
*A61K 31/445* (2006.01)
*C07D 277/08* (2006.01)
*C07D 417/02* (2006.01)

(52) U.S. Cl. .............. 514/326; 546/184; 546/192; 546/209; 548/146; 548/182; 548/183; 514/315; 514/365; 514/369

(58) Field of Classification Search .............. 548/146, 548/182, 183; 546/184, 192, 207, 209; 514/315, 514/317, 326, 365, 369
See application file for complete search history.

(56) References Cited

U.S. PATENT DOCUMENTS

| 4,552,891 | A | * | 11/1985 | Ho et al. ................. 514/443 |
| 5,208,250 | A | * | 5/1993 | Cetenko et al. ........... 514/369 |
| 5,362,733 | A | * | 11/1994 | Backstrom et al. ........ 514/270 |
| 5,464,856 | A | * | 11/1995 | Cetenko et al. ........... 514/389 |
| 5,889,037 | A | * | 3/1999 | Backstrom et al. ........ 514/389 |
| 6,121,303 | A | * | 9/2000 | Backstrom et al. ........ 514/389 |
| 6,673,816 | B1 | * | 1/2004 | Esswein et al. ........... 514/326 |
| 7,026,343 | B2 | | 4/2006 | Prochownik et al. |

OTHER PUBLICATIONS

Wang et al (2003): STN International HCAPLUS database, (Columbus, Ohio), Accession No. 2003:97274.*
Cetenko et al (1990): STN International HCAPLUS database, (Columbus, Ohio), Accession No. 1990:235298.*
Solow-Cordero et al (2004): STN International HCAPLUS database, (Columbus, Ohio), Accession No. 2004:703129.*
Aamlid et al (1989): STN International HCAPLUS database, (Columbus, Ohio), Accession No. 1989:227493.*
Hanefeld et al (1993): STN International HCAPLUS database, (Columbus, Ohio), Accession No. 1994:217393.*

Bazarov AV et al. A modest reduction in c-myc expression has minimal effects on cell growth and apoptosis but dramatically reduces susceptibility to Ras and Raf transformation. Cancer Res. Feb. 1, 2001;61(3):1178-86.
Berg T, et al. Small-molecule antagonists of Myc/Max dimerization inhibit Myc-induced transformation of chicken embyro fibroblasts. Proc Natl Acad Sci U S A. Mar. 19, 2002;99(6):3830-5.
Brodeur GM. Molecular pathology of human neuroblastomas. Semin Diagn Pathol. May 1994;11(2):118-25.
Cutshall NS, O'Day C, Prezhdo M. Rhodanine derivatives as inhibitors of JSP-1. Bioorg Chem Med Lett. Jul. 2005;15(14) 3374-9.
Dang CV. c-Myc target genes involved in cell growth, apoptosis, and metabolism. Mol Cell Biol. Jan. 1999;19(1):1-11.
Davis AC, et al. A null c-myc mutation causes lethality before 10.5 days of gestation in homozygotes and reduced fertility in heterozygous female mice. Genes Dev. Apr. 1993;7(4):671-82.
de Alboran IM et al. Analysis of C-MYC function in normal cells via conditional gene-targeted mutation. Immunity. Jan. 2001;14(1):45-55.
DuHadaway JB et al. Immunohistochemical analysis of Bin1/Amphiphysin II in human tissues: diverse sites of nuclear expression and losses in prostate cancer. J Cell Biochem. Feb. 15, 2003;88(3):635-42.
Eagle LR, Yin X, Brothman AR, Williams BJ, Atkin NB, Prochownik EV. Mutation of the MXI1 gene in prostate cancer. Nat Genet. Mar. 1995;9(3):249-55.
El Gedaily A et al. Discovery of new DNA amplification loci in prostate cancer by comparative genomic hybridization. Prostate. Feb. 15, 2001;46(3):184-90.
Felsher DW, Bishop JM. Reversible tumorigenesis by MYC in hematopoietic lineages. Mol Cell. Aug. 1999;4(2):199-207.
Felsher DW. Reversibility of oncogene-induced cancer. Curr Opin Genet Dev. Feb. 2004;14(1):37-42.
Fieber W et al. Structure, function, and dynamics of the dimerization and DNA-binding domain of oncogenic transcription factor v-Myc. J Mol Biol. Apr. 13, 2001;307(5):1395-410.
Flores I, Murphy DJ, Swigart LB, Knies U, Evan GI. Defining the temporal requirements for Myc in the progression and maintenance of skin neoplasia. Oncogene. Aug. 5, 2004;23(35):5923-30.
Ge K et al. Losses of the tumor suppressor BIN1 in breast carcinoma are frequent and reflect deficits in programmed cell death capacity. Int J Cancer. Feb. 1, 2000;85(3):376-83.
Giorello L et al. Inhibition of cancer cell growth and c-Myc transcriptional activity by a c-Myc helix 1-type peptide fused to an internalization sequence. Cancer Res. Aug. 15, 1998;58(16):3654-9.

(Continued)

*Primary Examiner*—Golam M Shameem
(74) *Attorney, Agent, or Firm*—Klarquist Sparkman, LLP

(57) ABSTRACT

Compounds and compositions for interfering with the association of Myc and Max are described herein. These compounds and compositions are useful in methods inhibiting growth or proliferation of a cell. Methods of inhibiting growth or proliferation of a cell are provided, comprising contacting the cell with an amount of a compound that interferes with Myc and Max association effective to inhibit growth or proliferation of the cell.

12 Claims, 12 Drawing Sheets

OTHER PUBLICATIONS

Gomez-Curet I, Perkins RS, Bennett R, Feidler KL, Dunn SP, Krueger LJ. c-Myc inhibition negatively impacts lymphoma growth. J Pediatr Surg. Jan. 2006;41(1):207-11.

Grandori C, Cowley SM, James LP, Eisenman RN. The Myc/Max/Mad network and the transcriptional control of cell behavior. Annu Rev Cell Dev Biol. 2000;16:653-99.

Huang MJ et al. A small-molecule c-Myc inhibitor, 10058-F4, induces cell-cycle arrest, apoptosis, and myeloid differentiation of human acute myeloid leukemia. Exp Hematol. Nov. 2006;34(11):1480-9.

Husain M, Sarveshwar IS. Synthesis & biodynamic activities of 5-(substituted benzylidene)- . . . -4-oxothiazolidine-2-thiones. Ind J Chem. 1985;24B:761-4.

Incles CM, Schultes CM, Neidle S. Telomerase inhibitors in cancer therapy: current status and future directions. Curr Opin Investig Drugs. Jun. 2003;4(6):675-85.

Jain M, Arvanitis C, Chu K, Dewy W, Leonhardt E, Trinh M, Sundberg CD, Bishop JM, Felsher DW. Sustained loss of a neoplastic phenotype by brief inactivation of MYC. Science. Jul. 5, 2002;297(5578):102-4.

Jenkins RB et al. Detection of c-myc oncogene amplification and chromosomal anomalies in metastatic prostatic carcinoma by fluorescence in situ hybridization. Cancer Res. Feb. 1, 1997;57(3):524-31.

Jung KC et al. Fatty acids, inhibitors for the DNA binding of c-Myc/Max dimer, suppress proliferation and induce apoptosis of differentiated HL-60 human leukemia cell. Leukemia. Jan. 2006;20(1):122-7.

Kaltz-Wittmer C et al. FISH analysis of gene aberrations (MYC, CCND1, ERBB2, RB, and AR) in advanced prostatic carcinomas before and after androgen deprivation therapy. Lab Invest. Sep. 2000;80(9):1455-64.

Kamijo T et al. Tumor suppression at the mouse INK4a locus mediated by the alternative reading frame product p19ARF. Cell. Nov. 28, 1997;91(5):649-59.

Karlssson A et al. Genomically complex lymphomas undergo sustained tumor regression upon MYC inactivation unless they acquire novel chromosomal translocations. Blood. Apr. 1, 2003;101(7):2797-803.

Khodair AI. A convenient synthesis of 2-arylidene-5H-thiazolo[2,3-b]quinazoline-3,5[2H]-diones and their benzoquinazoline derivatives. J Heterocycl Chem 2002;39(6)1153-60.

Kiessling A, Sperl B, Hollis A, Eick D, Berg T. Selective inhibition of c-Myc/Max dimerization and DNA binding by small molecules. Chem Biol. Jul. 2006;13(7):745-51.

Kleine-Kohlbrecher D, Adhikary S, Eilers M. Mechanisms of transcriptional repression by Myc. Curr Top Microbiol Immunol. 2006;302:51-62.

Kolly C et al. Proliferation, cell cycle exit, and onset of terminal differentiation in cultured keratinocytes . . . J Invest Dermatol. May 2005;124(5):1014-25. Erratum in: J. Invest Dermatol. Dec. 2006;126(12):2734.

Kumagai T et al. Eradication of Myc-overexpressing small cell lung cancer cells transfected with herpes simplex virus thymidine kinase gene containing Myc-Max . . . Cancer Res. Jan. 15, 1996;56(2):354-8.

Leglise MC, Dent GA, Ayscue LH, Ross DW. Leukemic cell maturation: phenotypic variability and oncogene expression in HL60 cells. Blood Cells. 1988;13(3):319-37.

Leonetti C et al. Antitumor effect of c-myc antisense phosphorothioate oligodeoxynucleotides on human melanoma cells in vitro and and in mice. J. Natl Cancer Inst. Apr. 3, 1996;88(7):419-29.

Lipinski C, Hopkins A. Navigating chemical space for biology and medicine. Nature. Dec. 16, 2004;432(7019):855-61.

Mateyak MK, Obaya AJ, Adachi S, Sedivy JM. Phenotypes of c-Myc-deficient rat fibroblasts isolated by targeted homologous recombination. Cell Growth Differ. Oct. 1997;8(10):1039-48.

McGuffie EM, Catapano CV. Design of a novel triple helix-forming oligodeoxyribonucleotide directed to the major promoter of the c-myc gene. Nucleic Acids Res. Jun. 15, 2002;30(12):2701-9.

Mo H, Henriksson M. Identification of small molecules that induce apoptosis in a Myc-dependent manner and inhibit Myc-driven transformation. Proc Natl Acad Sci U S A. Apr. 18, 2006;103(16):6344-9.

Nesbit CE, Tersak JM, Prochownik EV. MYC oncogenes and human neoplastic disease. Oncogene. May 13, 1999;18(19):3004-16.

Neumann CA et al. Essential role for the peroxiredoxin Prdx1 in erythrocyte antioxidant defence and tumour suppression. Nature. Jul. 31, 2003;424(6948):561-5.

Nilsson JA et al. Targeting ornithine decarboxylase in Myc-induced lymphomagenesis prevents tumor formation. Cancer Cell. May 2005;7(5):433-44.

Nupponen NN, Kakkola L, Koivisto P, Visakorpi T. Genetic alterations in hormone-refactory recurrent prostate carcinomas. Am J. Pathol. Jul. 1998;153(1):141-8.

Park SH, Raines RT. Fluorescence Polarization Assay to Quantify Protein-protein Interactions. Methods Mol Biol 2004;261:161-165 (2004).

Ponzielli R, Katz S, Barsyte-Lovejoy D, Penn LZ. Cancer therapeutics: targeting the dark side of Myc. Eur J Cancer. Nov. 2005;41(16):2485-501.

Prochownik EV et al. Commonly occurring loss and mutation of the MXI1 gene in prostate cancer. Genes Chromosomes Cancer. Aug. 1998;22(4):295-304.

Prochownik EV, VanAntwerp ME. Differential patterns of DNA binding by myc and max proteins. Proc Natl Acad Sci U S A. Feb. 1, 1993;90(3):960-4.

Prochownik EV. c-Myc as a therapeutic target in cancer. Expert Rev Anticancer Ther. Apr. 2004;4(2):289-302.

Qi Y, Gregory MA, Li Z, Brousal JP, West K, Hann SR. p19ARF directly and differentially controls the functions of c-Myc independently of p53. Nature. Oct. 7, 2004;431(7009):712-7.

Rothermund K et al. C-Myc-independent restoration of multiple phenotypes by two C-Myc target genes with overlapping functions. Cancer Res. Mar. 15, 2005;65(6):2097-107.

Schreiber-Agus N et al. Role of Mxi1 in ageing organ systems and the regulation of normal and neoplastic growth. Nature. Jun. 4, 1998;393(6684):483-7.

Yin X, Giap C, Lazo JS, Prochownik EV. Low molecular weight inhibitors of Myc-Max interaction and function. Oncogene. Sep. 18, 2003;22(40):6151-9.

Zhang H, Fan S. Prochownik EV. Distinct roles for MAX protein isoforms in proliferation and apoptosis. J Biol Chem. Jul. 11, 1997;272(28):17416-24.

Cole MD, Nikiforov MA. Transcriptional activation by the Myc oncoprotein. Curr Top Microbiol Immunol. 2006;302:33-50.

\* cited by examiner

10058-F4     12RH-NCN-1     28RH-NCN-1

Time ( Days)

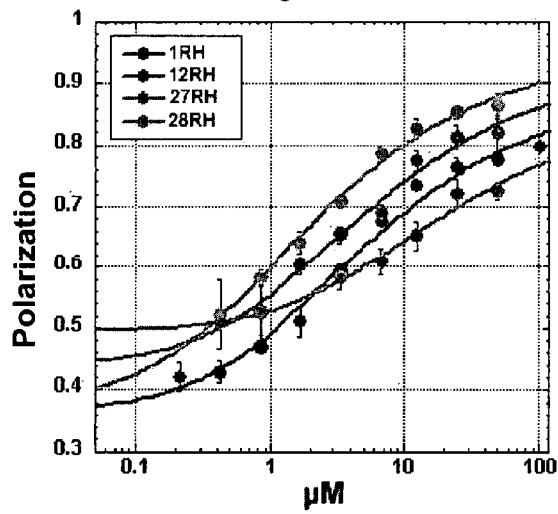
Fig. 6A
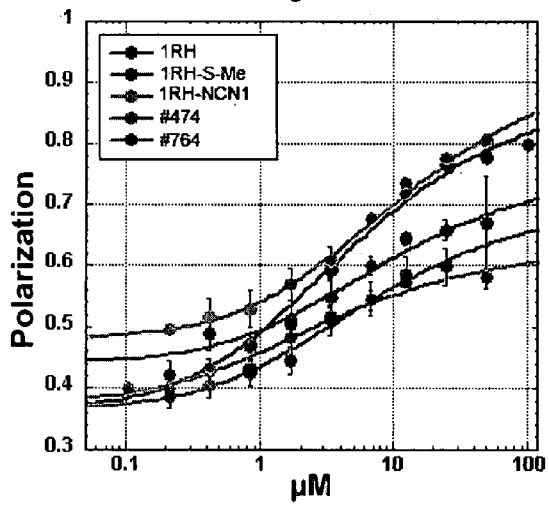
Fig. 6B
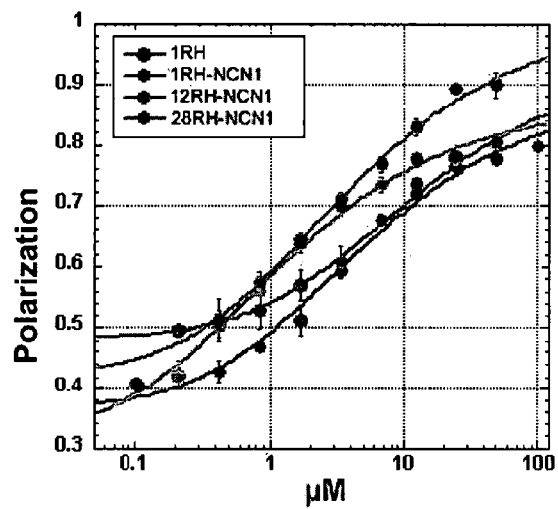
Fig. 6C
| Compound | $K_{Obs}$ (μM) |
|---|---|
| 1RH (10058-F4) | 2.3 ±0.7 |
| 12RH | 2.5 ±1.1 |
| 27RH | 8.6 ±3.7 |
| 28RH | 1.0 ±0.4 |
| 1RH-S-Me | 4.1 ±2.6 |
| #764 | 3.1 ±1.1 |
| #474 | 1.4 ±0.6 |
| 1RH-NCN1 | 5.7 ±0.8 |
| 12RH-NCN1 | 0.6 ±0.2 |
| 28RH-NCN1 | 1.8 ±0.5 |
Fig. 6D

LOW MOLECULAR WEIGHT MYC-MAX INHIBITORS

CROSS REFERENCE TO RELATED APPLICATIONS

This application claims the benefit under 35 U.S.C. §119 (e) to U.S. Provisional Patent Application No. 60/774,501, filed Feb. 17, 2006, which is incorporated herein by reference in its entirety.

STATEMENT REGARDING FEDERAL FUNDING

This invention was made with government support under Department of Defense, Grant No. PC030977. The government has certain rights in this invention.

Over the last several years, numerous approaches have been employed to inhibit the expression or function of the c-Myc oncoprotein, which is frequently over-expressed in human cancers. Through its role as a general basic-helix-loop-helix-leucine zipper (bHLH-LZ) transcription factor, c-Myc regulates hundreds of downstream target genes. The products of many of these promote transformation and control other aspects of the "c-Myc phenotype" by virtue of their effects on growth, metabolism, proliferation, apoptosis, and differentiation.

There exists overwhelming evidence implicating c-Myc in the pathogenesis, evolution, and/or survival of many human cancers, and that its therapeutic targeting would be beneficial. This evidence derives from five different types of studies:

c-MYC deregulation in cancer: c-Myc, or its close relative N-Myc, is over-expressed or otherwise deregulated in a variety of cancers. In some cases, a correlation between the degree of over-expression and tumor stage or survival has been demonstrated (Nesbit, C. E., Tersak, J. M. and Prochownik, E. V., MYC oncogenes and human neoplastic disease. Oncogene, 1999. 18: 3004-16; Jenkins, R. B., Qian, J., Lieber, M. M., Bostwick, D. G. Detection of c-myc oncogene amplification and chromosomal anomalies in metastatic prostatic carcinoma by fluorescence in situ hybridization. Cancer Res, 1997. 57: 524-31; Nupponen, N. N., Kakkola, L., Koivisto, P., Visakorpi, T. Genetic alterations in hormone-refractory recurrent prostate carcinomas. Am J Pathol, 1998. 153: 141-8; Kaltz-Wittmer, C., Klenk, Ulrich, Glaessgen, A., Aust, D. E., Diebold, J., Lohrs, U., Baretton, G. B. FISH analysis of gene aberrations (MYC, CCND1, ERBB2, RB, and AR) in advanced prostatic carcinomas before and after androgen deprivation therapy. Lab Invest, 2000. 80: 1455-64; El Gedaily, A., Bubendorf, L., Willi, N., Fu, W., Richter, J., Moch, H., Mihatsch, M. J., Sauter, G., Gasser, T. C. Discovery of new DNA amplification loci in prostate cancer by comparative genomic hybridization. Prostate, 2001. 46: 10-14 and Brodeur, G. M. Molecular pathology of human neuroblastomas. Semin Diagn Pathol, 1994. 11:118-25).

Inactivation of negative regulators of c-Myc is common in human cancers: We have demonstrated that Mxi1, a member of the Mad family, is deleted in nearly half of prostate cancers and, in some cases, is associated with mutational inactivation of the non-deleted allele (Eagle, L. R., Yin, X., Brothman, A. R., Williams, B. J., Atkin, N. B., Prochownik, E. V. Mutation of the MXI1 gene in prostate cancer. Nat Genet, 1995. 9: 249-55 and Prochownik, E. V., Eagle, Grove L., Deubler, D., Zhu, X. L., Stephenson, R. A., Rohr, L. R., Yin, X., Brothman, A. R. Commonly occurring loss and mutation of the MXI1 gene in prostate cancer. Genes Chromosomes Cancer, 1998. 22: 295-304). Bin1, a protein that interacts with and inhibits the transcriptional regulatory domain (TRD) of c-Myc, is also inactivated or deleted in a significant fraction of prostate and breast cancers (Ge, K., Duhadaway, J., Sakamuro, D., Wechsler-Reya, R., Reynolds, C., Prendergast, G. C. Losses of the tumor suppressor BIN1 in breast carcinoma are frequent and reflect deficits in programmed cell death capacity. Int J Cancer, 2000. 85:376-83 and DuHadaway, J. B., Lynch, F. J., Brisbay, S., Bueso-Ramos, C., Troncoso, P., McDonnell, T., Prendergast, G. C. Immunohistochemical analysis of Bin1/Amphiphysin II in human tissues: diverse sites of nuclear expression and losses in prostate cancer. J Cell Biochem, 2003. 88:635-42). More recently, the tumor suppressor $p19^{ARF}$ has been shown to interact with the c-Myc TRD and thus modulate its target gene induction and transforming activities (Qi, Y., Gregory, M. A., Li, Z., Brousal, J. P., West, K., Hann, S. R. p19ARF directly and differentially controls the functions of c-Myc independently of p53. Nature, 2004. 431:712-7).

Animal models: A number of animal models have demonstrated that the deregulated expression of c-Myc leads to the eventual emergence of a variety of clonal malignancies. The engineered knockouts of c-Myc negative regulators, including Mxi1, $p19^{ARF}$, and prdx1 also result in an increased cancer incidence, presumably as a consequence of the functional up-regulation of c-Myc (Kamijo, T., Zindy, F., Roussel, M. F., Quelle, D. E., Downing, J. R., Ashmun, R. A., Grosveld, G., Sherr, C. J. Tumor suppression at the mouse INK4a locus mediated by the alternative reading frame product p19ARF. Cell, 1997. 91:649-59; Schreiber-Agus, N., Meng, Y., Hoang, T., Hou J R., H., Chen, K., Gree3nberg, R., Cordon-Cardo, C., Lee, H. W., Depinho, R. A. Role of Mxi1 in ageing organ systems and the regulation of normal and neoplastic growth. Nature, 1998. 393: 483-7 and Neumann, C. A., Krause, D. S., Carman, C. V., Das, S., Dubey, D. P., Abraham, J. L., Bronson, R. T., Fujiwara, Y., Orkin, S. H., Van Etten, R. A. Essential role for the peroxiredoxin Prdx1 in erythrocyte antioxidant defence and tumour suppression. Nature, 2003; 424: 561-5).

The role of Myc in cell cycle progression, survival, and transformation by other oncogenes. The c-Myc knockout animal is an embryonic lethal and primary fibroblasts from such animals do not survive in vitro (Davis, A. C., Wims, M., Spotts, G. D., Hann, S. R., Bradley, A. A null c-myc mutation causes lethality before 10.5 days of gestation in homozygotes and reduced fertility in heterozygous female mice. Genes Dev, 1993. 7:671-82). Conditional inactivation of c-Myc in primary cells leads to immediate growth cessation and apoptosis (de Alboran, I. M., O'Hagan, R. C., Gartner, F., Malynn, B., Davidson, L., Rickert, R., Rajewsky, K., DePinho, R. A., Alt, F. W. Analysis of C-MYC function in normal cells via conditional gene-targeted mutation. Immunity, 2001. 14:45-55); even a 50% reduction of c-Myc in fibroblasts inhibits their transformation by other oncogenes by >90% without affecting proliferation (Bazarov, A. V., Adachi, Susumu, Li, S. F., Mateyak, M. K., Wei, S., Sedivy, J. M. A modest reduction in c-myc expression has minimal effects on cell growth and apoptosis but dramatically reduces susceptibility to Ras and Raf transformation. Cancer Res, 2001. 61: 1178-86). Therefore it can be argued that even if c-Myc were not directly involved in a specific tumor's etiology, its targeting might still result in a cellular environment that was less conducive to supporting a number of oncogene-dependent pathways.

Transient inhibition of c-Myc may be sufficient to achieve therapeutic effect. Transient inhibition of c-Myc can lead to tumor regression, as shown by Felsher and his colleagues utilizing tetracycline-regulatable Myc models of lymphoma and osteosarcoma (Felsher, D. W., Bishop, J. M. Reversible tumorigenesis by MYC in hematopoietic lineages. Mol Cell, 1999. 4:199-207; Jain, M., Arvanitis, C., Chu, K., Dewey, W., Leonhardt, E., Trinh, M., Sundberg, C. D., Bishop J. M., Felsher D. W. Sustained loss of a neoplastic phenotype by brief inactivation of MYC. Science, 2002. 297:102-104;

Karlsson, A., Giuriato, S., Tang, F., Fung-Weier, J., Levan, G., Felsher, D. W. Genomically complex lymphomas undergo sustained tumor regression upon MYC inactivation unless they acquire novel chromosomal translocations. Blood, 2003. 101:2797-803). These c-Myc-dependent tumors regress and undergo apoptosis following c-Myc silencing. Unexpectedly, rather than leading to tumor re-growth, the re-induction of c-Myc leads to massive apoptosis in 80% of cases. These findings suggest that even transient inhibition of c-Myc might be both therapeutically successful and desirable.

In summary, current evidence favors the notion that c-Myc deregulation is critical for tumorigenesis, thus making this oncoprotein an attractive therapeutic target. The possibility that transient inhibition of c-Myc might be even more effective than long-term inhibition must also be given serious consideration.

Specific inhibition of c-Myc is thus a major therapeutic goal. Among the direct approaches taken to inhibit c-Myc have been the use of triplex-forming oligonucleotides, which interfere with cMYC gene transcription, and anti-sense oligonucleotides, which either promote c-Myc mRNA degradation or inhibit its translation (McGuffie E M, Catapano C V. Design of a novel triple helix-forming oligodeoxyribonucleotide directed to the major promoter of the c-myc gene. Nucleic Acids Res 2002; 30:2701-9 and Leonetti C, D'Agnano I, Lozupone F, Valentini A, Geiser T, Zon G, et al. Antitumor effect of c-myc antisense phosphorothioate oligodeoxynucleotides on human melanoma cells in vitro and in mice. J Natl Cancer Inst 1996; 88:419-29). Indirect approaches have included the specific inhibition of downstream c-Myc target genes (Incles C M, Schultes C M, Neidle S. Telomerase inhibitors in cancer therapy: current status and future directions. Curr Opin Investig Drugs 2003; 4:675-85 and Nilsson J A, Keller U B, Baudino T A, Yang C, Norton S, Old J A, et al. Targeting ornithine decarboxylase in Myc-induced lymphomagenesis prevents tumor formation. Cancer Cell 2005; 7:433-44) and "suicide" vectors encoding cytotoxic proteins under the control of c-Myc-responsive promoters (Kumagai T, Tanio Y, Osaki T, Hosoe S, Tachibana I, Ueno K, et al. Eradication of Myc-overexpressing small cell lung cancer cells transfected with herpes simplex virus thymidine kinase gene containing Myc-Max response elements. Cancer Res 1996; 56:354-8). Despite some successes, most of these approaches continue to be hampered by technical difficulties pertaining largely to delivery and the fact that many transforming c-Myc target genes are functionally redundant and/or cell type-specific (Prochownik E V. c-Myc as a therapeutic target in cancer. Expert Rev Anticancer Ther 2004; 4: 289-302).

More recently, we and others have employed a different approach that utilizes low molecular weight compounds (hereafter referred to as "Myc-Max compounds") to inhibit or reverse the association between c-Myc and its obligate bHLH-LZ heterodimerization partner, Max (Berg T, Cohen S B, Desharnais J, Sonderegger C, Maslyar D J, Goldberg J, et al. Small-molecule antagonists of Myc/Max dimerization inhibit Myc-induced transformation of chicken embryo fibroblasts. Proc Natl Acad Sci USA. 2002; 99:3830-5, Yin X, Giap C, Lazo J S, Prochownik E V. Low molecular weight inhibitors of Myc-Max interaction and function. Oncogene 2003; 22:6151-9 and U.S. Pat. No. 7,026,343). In its transcriptionally active form, the c-Myc-Max heterodimer binds specifically to canonical DNA sequences termed E-boxes, which are usually located within the proximal promoters or first introns of positively-regulated c-Myc target genes (Cole M D, Nikiforov M A. Transcriptional activation by the Myc oncoprotein. Curr Top Microbiol Immunol 2006; 302:33-50 and Grandori C, Cowley S M, James L P, Eisenman R N. The Myc/Max/Mad network and the transcriptional control of cell behavior. Annu Rev Cell Dev Biol 2000; 16:653-99). Negative gene regulation by c-Myc, also requires Max, although DNA binding occurs at non-E-box-containing InR elements located at transcriptional initiation sites (Kleine-Kohlbrecher D, Adhikary S, Eilers M. Mechanisms of transcriptional repression by Myc. Curr Top Microbiol Immunol 2006; 302: 51-62). Thus, Myc-Max compounds not only abrogate protein heterodimerization and DNA binding by c-Myc-Max but all subsequent downstream functions as well.

The major problem with all Myc-Max compounds described thus far, which limits their clinical utility, is their relatively low potencies, with significant inhibition of tumor cell growth being obtained only with concentrations in the range of 50-100 µM. We have therefore attempted in the current work to utilize a directed chemical design approach as a means of identifying novel analogs with improved efficacies.

SUMMARY

Compounds and compositions for interfering with the association of Myc and Max are described herein. These compounds and compositions are useful in methods inhibiting growth or proliferation of a cell. Methods of inhibiting growth or proliferation of a cell are provided, comprising contacting the cell with an amount of a compound that interferes with Myc and Max association effective to inhibit growth or proliferation of the cell.

In one non-limiting embodiment, a compound is provided having the structure (Formula I):

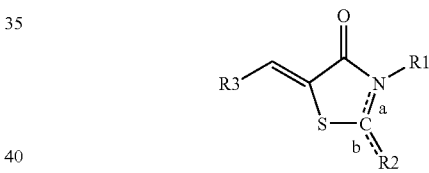

wherein R1 is H, alkyl, 5-6 atom heterocyclicgroup, or is not present; R2 is O, S, $C_{1-3}$ alkoxyl group, or $C_{1-3}$ alkylthiyl group; and R3 is one of phenyl, diphenyl, naphtyl, a substituted phenyl, cylcohexyl, a substituted cyclohexyl, wherein the substituted phenyl comprises one or more of: a 2-, 3-, 4-, or 5-halide; a 3-, 4-, or 5-nitro group; a 3-, 4-, or 5-cyano group; a 3-, 4-, or 5-acyl group; a 3-, 4-, or 5-carboxyl group; a 3-, 4-, or 5-hydroxyl group; a 3-, 4-, 5-$C_{1-3}$ alkoxyl group; a $C_{1-4}$ saturated or unsaturated alkyl group; and wherein the substituted cyclohexyl comprises one of: a 3-, 4-, or 5-halide; a 3-, 4-, 5-$C_{1-3}$ alkoxyl group; and a $C_{1-4}$ saturated or unsaturated alkyl group and a and/or b are single or double bonds, wherein when R1 is H and R2 is S, R3 is not 4-ethyl phenyl, or a pharmaceutically acceptable salt thereof. In all embodiments, if present, the heterocyclic group can be one of

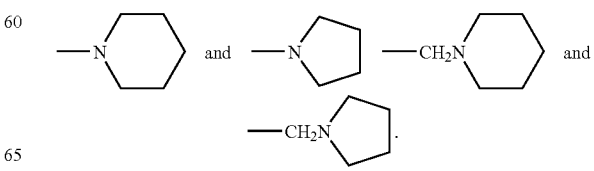

In another non-limiting embodiment, the compound has the structure:

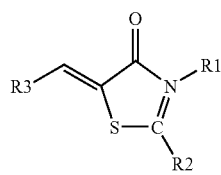

wherein R2 is $C_{1-3}$ alkoxyl group or $C_{1-3}$ alkylthiyl group; and R3 is one of phenyl, diphenyl, naphtyl, a substituted phenyl, cylcohexyl, a substituted cyclohexyl, wherein the substituted phenyl comprises one or more of: a 2-, 3-, 4-, or 5-halide; a 3-, 4-, or 5-nitro group; a 3-, 4-, or 5-cyano group; a 3-, 4-, or 5-acyl group; a 3-, 4-, or 5-carboxyl group; a 3-, 4-, or 5-hydroxyl group; a 3-, 4-, 5-$C_{1-3}$ alkoxyl group; a $C_{1-4}$ saturated or unsaturated alkyl group; and wherein the substituted cyclohexyl comprises one of: a 3-, 4-, or 5-halide; a 3-, 4-, 5-$C_{1-3}$ alkoxyl group; and a $C_{1-4}$ saturated or unsaturated alkyl group.

In yet another non-limiting embodiment, the compound has the structure:

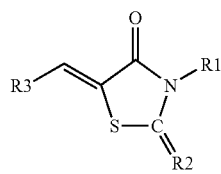

wherein R1 is H, alkyl, or a 5-6 atom heterocyclicgroup; R2 is O or S; and R3 is one of phenyl, diphenyl, naphtyl, a substituted phenyl, cylcohexyl, a substituted cyclohexyl, wherein the substituted phenyl comprises one or more of: a 2-, 3-, 4-, or 5-halide; a 3-, 4-, or 5-nitro group; a 3-, 4-, or 5-cyano group; a 3-, 4-, or 5-acyl group; a 3-, 4-, or 5-carboxyl group; a 3-, 4-, or 5-hydroxyl group; a 3-, 4-, 5-$C_{1-3}$ alkoxyl group; a $C_{1-4}$ saturated or unsaturated alkyl group; and wherein the substituted cyclohexyl comprises one of: a 3-, 4-, or 5-halide; a 3-, 4-, 5-$C_{1-3}$ alkoxyl group; and a $C_{1-4}$ saturated or unsaturated alkyl group, wherein when R1 is H and R2 is S, R3 is not 4-ethyl phenyl, or a pharmaceutically acceptable salt thereof.

In another non-limiting embodiment, the compound has the structure:

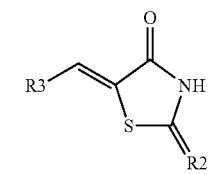

wherein R2 is O or S; and R3 is one of phenyl, diphenyl, naphtyl, a substituted phenyl, cylcohexyl, a substituted cyclohexyl, wherein the substituted phenyl comprises one or more of: a 2-, 3-, 4-, or 5-halide; a 3-, 4-, or 5-nitro group; a 3-, 4-, or 5-cyano group; a 3-, 4-, or 5-acyl group; a 3-, 4-, or 5-carboxyl group; a 3-, 4-, or 5-hydroxyl group; a 3-, 4-, 5-$C_{1-3}$ alkoxyl group; a $C_{1-4}$ saturated or unsaturated alkyl group; and wherein the substituted cyclohexyl comprises one of: a 3-, 4-, or 5-halide; a 3-, 4-, 5-$C_{1-3}$ alkoxyl group; and a $C_{1-4}$ saturated or unsaturated alkyl group, wherein when R2 is S, R3 is not 4-ethyl phenyl, or a pharmaceutically acceptable salt thereof.

In certain non-limiting embodiments, R3 is a substituted phenyl or a substituted cyclohexyl group comprising a 2-, 3-, 4-, or 5-halide group, such as a chlorine or fluorine, or, more specifically one of 4-chloro and 4-fluoro; a 3-, 4-, or 5-nitro group, such as 4-nitro; a 3-, 4-, or 5-cyano group, such as 4-cyano; a 3-, 4-, or 5-acyl group, such as 4-acyl; a 3-, 4-, or 5-carboxyl group; such as 4-carboxyl; one or more 3-, 4-, or 5-hydroxyl groups, such as 3, 4 dihydroxy; a 3-, 4-, or 5-$C_{1-3}$ alkoxyl group, such as 3-ethoxyl, 5-ethoxyl or 4-methoxyl; a $C_{1-4}$ saturated alkyl group, such as a propyl group, an isopropyl group, a butyl group, an isobutyl group, 2-, 3-, 4-, 5- or chosen from one of 2-Rh, 4-Rh, 5-Rh, 6-Rh, 9-Rh, 12-Rh, 13-Rh, 14-Rh, 16-Rh, 22-Rh, 23-Rh, 27-Rh, 28-Rh, 30-Rh, 32-Rh, 12RH-NCN-1 and 28RH-NCN-1.

In yet another non-limiting embodiment, the compound has the structure:

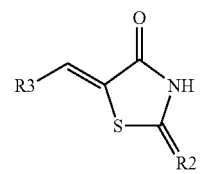

wherein R2 is O or S and R3 is one of phenyl, a substituted phenyl, diphenyl, cyclohexyl or a substituted cyclohexyl, wherein the substituted phenyl comprises one or more of: a 3-, 4-, or 5-halide; a 3-, 4- or 5-$C_{1-3}$ alkoxyl group; and a $C_{1-4}$ saturated or unsaturated alkyl group, and wherein the substituted cyclohexyl comprises one or more of: a 3-, 4-, or 5-halide; a 3-, 4- or 5-$C_{1-3}$ alkoxyl group; and a $C_{1-4}$ saturated or unsaturated alkyl group, wherein when R2 is S, R3 is not 4-ethyl phenyl, or a pharmaceutically acceptable salt thereof.

In any embodiment of the compound described herein, the compound may be a pharmaceutically acceptable salt, including, without limitation, one of an inorganic acid salt, an organic acid salt and a basic salt. Non-limiting examples of salts include hydrochloric acid salts, hydrobromic acid salts, phosphoric acid salts, metaphosphoric acid salts, nitric acid salts, sulfuric acid salts, acetic acid salts, benzenesulfonic acid salts, benzoic acid salts, citric acid salts, ethanesulfonic acid salts, fumaric acid salts, gluconic acid salts, glycolic acid salts, isethionic acid salts, lactic acid salts, lactobionic acid salts, maleic acid salts, malic acid salts, methanesulfonic acid salts, succinic acid salts, p-toluenesulfonic acid salts, tartaric acid salts, ammonium salts salts, alkali metal salts, alkaline earth metal salts, trometamol (2-amino-2-hydroxymethyl-1, 3-propanediol) salts, diethanolamine salts, lysine salts or ethylenediamineone salts.

Also provided herein is a composition comprising an active ingredient (drug, compound) and a pharmaceutically-acceptable excipient. In one non-limiting embodiment, the compound has the structure:

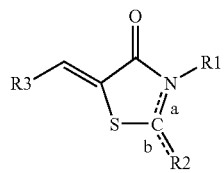

wherein R1 is H, alkyl, 5-6 atom heterocyclicgroup, $C_{1-4}$ saturated or unsaturated alkyl group, an ester-containing group having 2-8 carbon atoms, or not present; R2 is O, S, $C_{1-3}$ alkoxyl group, or $C_{1-3}$ alkylthiyl group; and R3 is one of phenyl, diphenyl, naphtyl, a substituted phenyl, cylcohexyl, a substituted cyclohexyl, wherein the substituted phenyl comprises one or more of: a 2-, 3-, 4-, or 5-halide; a 3-, 4-, or 5-nitro group; a 3-, 4-, or 5-cyano group; a 3-, 4-, or 5-acyl group; a 3-, 4-, or 5-carboxyl group; a 3-, 4-, or 5-hydroxyl group; a 3-, 4-, 5-$C_{1-3}$ alkoxyl group; a $C_{1-4}$ saturated or unsaturated alkyl group; and an extended R4 group connected to the R3 group through an ether- or polyoxyethylene-derived linkage; and wherein the substituted cyclohexyl comprises one of: a 3-, 4-, or 5-halide; a 3-, 4-, 5-$C_{1-3}$ alkoxyl group; and a $C_{1-4}$ saturated or unsaturated alkyl group and a and/or b are single or double bonds, wherein when R1 is H and R2 is S, R3 is not 4-ethyl phenyl, or a pharmaceutically acceptable salt thereof, in an amount effective to interfere with c-Myc and Max association effective to inhibit growth or proliferation of the cell, and a pharmaceutically acceptable excipient. In certain non-limiting, embodiments, R1 is a $C_{1-4}$ saturated or unsaturated alkyl group, such as a 2-propynyl group or a 2-propenyl group. In other embodiments, R1 comprises from 1-8 carbon atoms and an ester group, for example and without limitation, one of —$(CH_2)$—$(COO)$—$CH_3$ and —$(CH_2)_2$—$(COO)$—$(CH_2)_3CH_3$. In other embodiments, R1 is one of R1 is one of one of

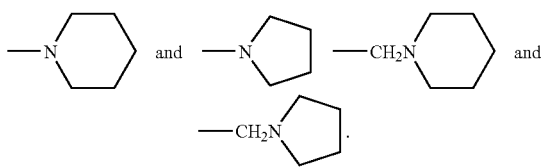

In certain non-limiting embodiments, R3 has the structure R4-R5-R6, wherein R4 is phenyl, 2-, 3-, 4-, or 5-halide-substituted phenyl, 2-, 3-, 4-, or 5-nitro-substituted phenyl or 3-, 4-, 5-$C_{1-3}$ alkoxyl-substituted phenyl; R5 is a $C_{1-4}$ ether-bond-containing linkage and R6 is phenyl or $C_{1-3}$ alkane-substituted phenyl. For example and without limitation, the ether linkage may be —O—$[CH_2—CH_2—O]_n$, where n is 1 or 2. R3 also may be a 2-, 3-, 4-, or 5-halide-substituted phenyl or cyclohexyl group. The halide may be chloride or fluoride, such as 2-fluoro. R3 may be a 3-, 4-, 5-$C_{1-3}$ alkoxyl group-substituted phenyl or cyclohexyl group, where the 3-, 4-, 5-$C_{1-3}$ alkoxyl group can be, for example, 3-methoxyl. In other embodiments, R3 is a $C_{1-4}$ saturated or unsaturated alkyl group-substituted phenyl or cyclohexyl group wherein, for example the $C_{1-4}$ saturated or unsaturated alkyl group is chosen from an ethyl or methyl group. Specific non-limiting examples of the compound are: 3584-0104, 3584-0372, 015, 6123474, 6863764, 3584-0476, 3584-0791, 2-Rh, 4-Rh, 5-Rh, 6-Rh, 9-Rh, 12-Rh, 13-Rh, 14-Rh, 16-Rh, 22-Rh, 23-Rh, 27-Rh, 28-Rh, 30-Rh, 32-Rh, 12RH-NCN-1 and 28RH-NCN-1.

The composition may comprise a pharmaceutically-acceptable salt of the compound, for example and without limitation, one of an inorganic acid salt, an organic acid salt and a basic salt. Non-limiting examples of pharmaceutically-acceptable salts include: hydrochloric acid salts, hydrobromic acid salts, phosphoric acid salts, metaphosphoric acid salts, nitric acid salts, sulfuric acid salts, acetic acid salts, benzenesulfonic acid salts, benzoic acid salts, citric acid salts, ethanesulfonic acid salts, fumaric acid salts, gluconic acid salts, glycolic acid salts, isethionic acid salts, lactic acid salts, lactobionic acid salts, maleic acid salts, malic acid salts, methanesulfonic acid salts, succinic acid salts, p-toluenesulfonic acid salts, tartaric acid salts, ammonium salts, alkali metal salts, alkaline earth metal salts, trometamol (2-amino-2-hydroxymethyl-1,3-propanediol) salts, diethanolamine salts, lysine salts or ethylenediamineone salts.

Also provided is a method of inhibiting growth or proliferation of a cell, comprising contacting the cell with an amount of a compound that interferes with c-Myc and Max association effective to inhibit growth or proliferation of the cell. In one non-limiting example, the compound has the formula:

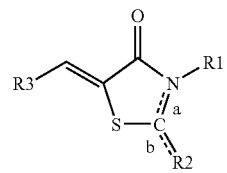

wherein R1 is H, alkyl, $C_{3-6}$ heterocyclic group, $C_{1-4}$ saturated or unsaturated alkyl group, ester-derived group, or not present; R2 is O, S, $C_{1-3}$ alkoxyl group, or $C_{1-3}$ alkylthiyl group; and R3 is one of phenyl, diphenyl, naphtyl, a substituted phenyl, cylcohexyl, a substituted cyclohexyl, wherein the substituted phenyl comprises one or more of: a 2-, 3-, 4-, or 5-halide; a 3-, 4-, or 5-nitro group; a 3-, 4-, or 5-cyano group; a 3-, 4-, or 5-acyl group; a 3-, 4-, or 5-carboxyl group; a 3-, 4-, or 5-hydroxyl group; a 3-, 4-, 5-$C_{1-3}$ alkoxyl group; a $C_{1-4}$ saturated or unsaturated alkyl group other than 4-ethyl; and an extended R4 group connected to the R3 group through an ether- or polyoxyethylene-derived linkage; and wherein the substituted cyclohexyl comprises one of: a 3-, 4-, or 5-halide; a 3-, 4-, 5-$C_{1-3}$ alkoxyl group; and a $C_{1-4}$ saturated or unsaturated alkyl group and a and/or b are single or double bonds, or a pharmaceutically acceptable salt thereof, in an amount effective to interfere with c-Myc and Max association effective to inhibit growth or proliferation of the cell, and a pharmaceutically acceptable excipient.

In another non-limiting embodiment, the compound has the structure:

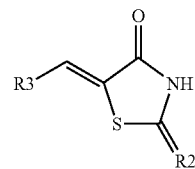

wherein R2 is O or S and R3 is one of phenyl, a substituted phenyl, diphenyl, cyclohexyl or a substituted cyclohexyl, wherein the substituted phenyl comprises one or more of: a 3-, 4-, or 5-halide; a 3-, 4- or 5-$C_{1-3}$ alkoxyl group; and a $C_{1-4}$ saturated or unsaturated alkyl group other than 4-ethyl, and wherein the substituted cyclohexyl comprises one or more of: a 3-, 4-, or 5-halide; a 3-, 4- or 5-$C_{1-3}$ alkoxyl group; and a $C_{1-4}$ saturated or unsaturated alkyl group, wherein when R2 is S, R3 is not 4-ethyl phenyl, or a pharmaceutically acceptable salt thereof. Specific non-limiting examples of the compound include one or more of: 3584-0104, 3584-0372, 015, 6123474, 6863764, 3584-0476, 3584-0791, 2-Rh, 4-Rh, 5-Rh, 6-Rh, 9-Rh, 12-Rh, 13-Rh, 14-Rh, 16-Rh, 22-Rh, 23-Rh, 27-Rh, 28-Rh, 30-Rh, 32-Rh, 12RH-NCN-1 and 28RH-NCN-1.

Also provided is a method of determining if a compound binds to c-Myc, comprising: determining by fluorescent polarization if the presence of a first amount of one of a Myc protein or a portion of Myc protein that contains a c-Myc bHLH-ZIP dimerization/DNA binding domain in a solution containing a fluorescent polarizing compound de-polarizes light to a different degree as a solution containing a different amount, or none of the Myc protein or portion thereof; determining by x-ray crystallography if a compound binds to c-Myc bHLH-LZ; or determining by NMR spectroscopy if a compound binds to c-Myc bHLH-LZ. In one embodiment, fluorescent polarization is used to determine if the compound binds to cMyc.

BRIEF DESCRIPTION OF THE DRAWINGS

FIG. 6 shows the results of fluorescence titration assays. Samples of inhibitor at two-fold dilutions, both in the absence and presence of c-Myc$_{353-439}$ were analyzed as described in reference to FIG. 5 and in Materials and Methods. FIG. 6A shows titrations for six-member ring-substituted compounds 12RH, 27RH, and 28RH. FIG. 6B shows titrations for rhodanine ring-substituted compounds 1RH-S-Me, #474, and #764. FIG. 6C shows titrations for third generation, dual-substituted compounds 1RH-NCN1, 12RH-NCN1, and 28RH-NCN1. The table in FIG. 6D provides calculated Kobs values based upon the above titration profiles. Note that in all cases the index compound 10058-F4 (1RH) was used as a control. Also note that compound #015 was not included in these and other fluorescence polarization assays due to its lack of fluorescence.

DETAILED DESCRIPTION

Figure 1A:
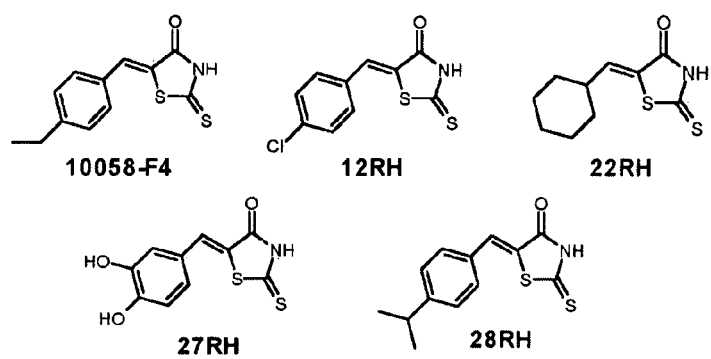
FIG. 1A provides structures of the 10058-F4 (1RH) index compound and the five most potent six-member ring analogs.

Compounds that selectively prevent or disrupt the association between the c-Myc oncoprotein and its obligate heterodimeric partner Max (Myc-Max compounds) have been previously identified by high-throughput screening of chemical libraries (see, U.S. Pat. No. 7,026,343). Although these agents specifically inhibit the growth of c-Myc-expressing cells, their clinical applicability is limited by their low potency. Described herein are several chemical modifications of one of these original compounds, 10058-F4, which result in significant improvements in efficacy. Compared to the parent structure, these analogs demonstrate enhanced growth inhibition of c-Myc-expressing cells in a manner that generally correlates with their ability to disrupt c-Myc-Max association. Furthermore, by use of a sensitive fluorescence polarization assay it is shown that both 10058-F4 and its active analogs bind specifically to monomeric c-Myc. These studies demonstrate that improved Myc-Max compounds can be generated by a directed approach involving deliberate modification of an index compound. They further show that the compounds specifically target c-Myc, which exists in a dynamic and relatively unstructured state with only partial and transient α-helical content.

The use of numerical values in the various ranges specified in this application, unless expressly indicated otherwise, are stated as approximations as though the minimum and maximum values within the stated ranges are both preceded by the word "about", whether or not the term "about" is present. In this manner, slight variations above and below the stated ranges can be used to achieve substantially the same results as values within the ranges. Also, unless indicated otherwise, the disclosure of these ranges is intended as a continuous range including every value between the minimum and maximum values. For definitions provided herein, those definitions also refer to word forms, cognates and grammatical variants of those words or phrases.

As used herein, and unless indicated otherwise, "a" and/or "an" refer to one or more.

As used herein, the term "comprising", is intended to be inclusive and/or open-ended and does not exclude additional, unrecited elements or method steps. The transitional phrase "consisting of" excludes any element, step, or ingredient not specified in the claim.

As used herein, "pharmaceutically acceptable," means acceptable for use in humans and animals. Excipients include, without limitation, one or more suitable: vehicle(s), solvent(s), diluent(s), pH modifier(s), buffer(s), salt(s), colorant(s), rheology modifier(s), lubricant(s), filler(s), antifoaming agent(s), erodeable polymer(s), hydrogel(s), surfactant(s), emulsifier(s), adjuvant(s), preservative(s), phospholipid(s), fatty acid(s), mono-, di- and tri-glyceride(s) and derivatives thereof, waxe(s), oil(s) and water. The choice of excipient depends on the dosage form in question. Parenteral administration may require at a minimum buffers and salts to match physiological conditions, and thus includes salt and buffer, such as, without limitation, normal saline or phosphate-buffered saline. Depending on the solubility of the compound (active ingredient), the dosage form would be aqueous, micellular (including liposomes) or lipophilic. Formulation of a drug product and choice of suitable excipient(s) with adequate bioavailability is within the average skill of those in the pharmaceutical and formulary arts. The compound may be administered via any useful delivery route, including, without limitation, orally or parenterally, and the drug product/dosage form is tailored to the desired delivery route. For example and without limitation, an HCl salt of a compound described herein may be administered intravenously or intramuscularly in normal saline, or may be administered in tablet or capsule form with appropriate excipients.

In any case, as used herein, any agent used for interfering with Myc and Max association is administered in an amount effective to slow or stop growth of a cell in an amount and in a dosage regimen effective to prevent, reduce the rate of cellular growth. As shown herein, dose-response curves indicate that, for example and without limitation, concentration ranges of from about 1 µM to about 50 µM of any given drug product may prove useful. Different excipients or reagent systems, dosage forms, administration routes and salt or freebase forms of the active ingredients would be expected to affect bioavailability and the specific activity of the active agent, and thus the ability of any given active ingredient to decrease cellular growth rates in an individual. Administration of different amounts or concentrations of the active ingredient using different dosage regimens will achieve similar results, with the drug product administered, typically and without limitation, from one to ten times daily, including 2, 3, 4, 5, 6, 7, 8, 9 and 10 times daily. The amount of the drug product administered to the patient, also may vary depending on the dosage form. A person of average skill in the pharmaceutical and medical arts will appreciate that it will be a matter of simple design choice and optimization to identify a suitable dosage regimen for treatment of any given disease state (e.g., cancer).

Pharmaceutically acceptable salts are, because their solubility in water is greater than that of the initial or basic compounds, particularly suitable for medical applications. These salts have a pharmaceutically acceptable anion or cation. Suitable pharmaceutically acceptable acid addition salts of the compounds of the invention include, without limitation, salts of inorganic acids such as hydrochloric acid, hydrobromic, phosphoric, metaphosphoric, nitric and sulfuric acid, and of organic acids such as, for example, acetic acid, benzenesulfonic, benzoic, citric, ethanesulfonic, fumaric, gluconic, glycolic, isethionic, lactic, lactobionic, maleic, malic, methanesulfonic, succinic, p-toluenesulfonic and tartaric acid. Suitable pharmaceutically acceptable basic salts include without limitation, ammonium salts, alkali metal salts (such as sodium and potassium salts), alkaline earth metal salts (such as magnesium and calcium salts), and salts of trometamol (2-amino-2-hydroxymethyl-1,3-propanediol), diethanolamine, lysine or ethylenediamine. Pharmaceutically acceptable salts may be prepared from parent compounds by any useful method, as are well known in the chemistry and pharmaceutical arts.

Dosage forms include, without limitation, tablets, capsules, liquids for injection, eyedrops (liquids), ointments, oils, multi-phase systems (such as, liposome, micellular, homogenates or suspensions of liquids or semi-solid or solid particles), gels, creams and transdermal devices.

A compound is provided having the ability to interfere with cMyc activity (without limitation, the association with Max) and thus the ability to reduce cell growth or proliferation for example and without limitation in a cancer or in psoriasis. According to one embodiment, the compound has the structure (Formula I):

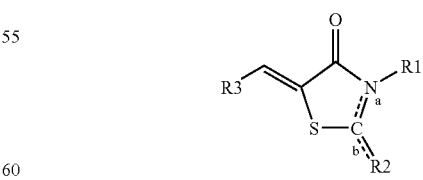

wherein R1 is H, alkyl, 5-6 atom heterocyclicgroup, or is not present; R2 is O, S, $C_{1-3}$ alkoxyl group (—O—$CH_3$, —O—$CH_2$—$CH_3$, —O—$CH_2$—$CH_2$—$CH_3$ or —O—$CH_2$—$(CH_3)_2$), or $C_{1-3}$ alkylthiyl group (—S—$CH_3$, —S—$CH_2$—$CH_3$, —S—$CH_2$—$CH_2$—$CH_3$ or —S—$CH_2$—

(CH₃)₂); and R3 is one of phenyl, diphenyl (having two linked phenyl groups attached by a linker, such as an ether-containing linker, for example —O—[CH₂—CH₂—O]ₙ—, where n is 1 or 2), naphtyl, a substituted phenyl, cylcohexyl and a substituted cyclohexyl. The substituted phenyl can comprise one or more of: a 2-, 3-, 4-, or 5-halide (such as, without limitation 4-fluoro or 4-chloro); a 3-, 4-, or 5-nitro group (such as, without limitation, 5-nitro); a 3-, 4-, or 5-cyano group (such as, without limitation,); a 3-, 4-, or 5-acyl group (such as, without limitation,); a 3-, 4-, or 5-carboxyl group (such as, without limitation,); a 3-, 4-, or 5-hydroxyl group (such as, without limitation,); a 3-, 4-, 5-C₁₋₃ alkoxyl group; a C₁₋₄ saturated or unsaturated alkyl group (methyl, ethyl, propyl, isopropyl, butyl, isobutyl and t-butyl); and wherein the substituted cyclohexyl comprises one of: a 3-, 4-, or 5-halide; a 3-, 4-, 5-C₁₋₃ alkoxyl group; and a C₁₋₄ saturated or unsaturated alkyl group and a and/or b are single or double bonds, wherein when R1 is H and R2 is S, R3 is not 4-ethyl phenyl (that is, the compound is not 10058-F4) or a pharmaceutically acceptable salt thereof. Specific, non-limiting examples of this compound include chosen from one of 2-Rh, 4-Rh, 5-Rh, 6-Rh, 9-Rh, 12-Rh, 13-Rh, 14-Rh, 16-Rh, 22-Rh, 23-Rh, 27-Rh, 28-Rh, 30-Rh, 32-Rh, 12RH-NCN-1 and 28RH-NCN-1.

A composition comprising a compound in an amount effective to reduce growth of a cell and a pharmaceutically-acceptable excipient also is provided. The compound is, according to one embodiment, a compound having the structure:

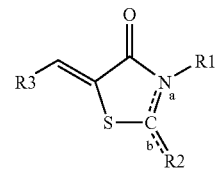

wherein R1 is H, alkyl, 5-6 atom heterocyclicgroup (such as, without limitation, one of

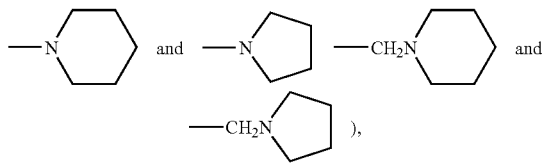

C₁₋₄ saturated or unsaturated alkyl group, an ester-containing group having 2-8 carbon atoms, or is not present; R2 is O, S, C₁₋₃ alkoxyl group, or C₁₋₃ alkylthiyl group; and R3 is one of phenyl, diphenyl, naphtyl, a substituted phenyl, cylcohexyl, a substituted cyclohexyl, wherein the substituted phenyl comprises one or more of: a 2-, 3-, 4-, or 5-halide; a 3-, 4-, or 5-nitro group; a 3-, 4-, or 5-cyano group; a 3-, 4-, or 5-acyl group; a 3-, 4-, or 5-carboxyl group; a 3-, 4-, or 5-hydroxyl group; a 3-, 4-, 5-C₁₋₃ alkoxyl group; a C₁₋₄ saturated or unsaturated alkyl group; and an extended R4 group connected to the R3 group through an ether- or polyoxyethylene-derived linkage; and wherein the substituted cyclohexyl comprises one of: a 3-, 4-, or 5-halide; a 3-, 4-, 5-C₁₋₃ alkoxyl group; and a C₁₋₄ saturated or unsaturated alkyl group and a and/or b are single or double bonds, wherein when R1 is H and R2 is S, R3 is not 4-ethyl phenyl or a pharmaceutically acceptable salt thereof. Specific, non-limiting examples of this compound include chosen from one of 3584-0104, 3584-0372, 015, 6123474, 6863764, 3584-0476, 3584-0791, 2-Rh, 4-Rh, 5-Rh, 6-Rh, 9-Rh, 12-Rh, 13-Rh, 14-Rh, 16-Rh, 22-Rh, 23-Rh, 27-Rh, 28-Rh, 30-Rh, 32-Rh, 12RH-NCN-1 and 28RH-NCN-1.

According to yet another embodiment, a method of inhibiting growth or proliferation of a cell, comprising contacting the cell with an amount of a compound that interferes with c-Myc and Max association effective to inhibit growth or proliferation of the cell, the compound having the formula:

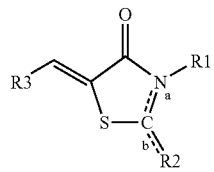

wherein R1 is H, alkyl, C₃₋₆ heterocyclic group, C₁₋₄ saturated or unsaturated alkyl group, ester-derived group, or not present; R2 is O, S, C₁₋₃ alkoxyl group, or C₁₋₃ alkylthiyl group; and R3 is one of phenyl, diphenyl, naphtyl, a substituted phenyl, cylcohexyl, a substituted cyclohexyl, wherein the substituted phenyl comprises one or more of: a 2-, 3-, 4-, or 5-halide; a 3-, 4-, or 5-nitro group; a 3-, 4-, or 5-cyano group; a 3-, 4-, or 5-acyl group; a 3-, 4-, or 5-carboxyl group; a 3-, 4-, or 5-hydroxyl group; a 3-, 4-, 5-C₁₋₃ alkoxyl group; a C₁₋₄ saturated or unsaturated alkyl group; and an extended R4 group connected to the R3 group through an ether- or polyoxyethylene-derived linkage; and wherein the substituted cyclohexyl comprises one of: a 3-, 4-, or 5-halide; a 3-, 4-, 5-C₁₋₃ alkoxyl group; and a C₁₋₄ saturated or unsaturated alkyl group and a and/or b are single or double bonds, wherein when R1 is H and R2 is S, R3 is not 4-ethyl phenyl or a pharmaceutically acceptable salt thereof, in an amount effective to interfere with c-Myc and Max association effective to inhibit growth or proliferation of the cell, and a pharmaceutically acceptable excipient. Specific, non-limiting examples of this compound include chosen from one of 3584-0104, 3584-0372, 015, 6123474, 6863764, 3584-0476, 3584-0791, 2-Rh, 4-Rh, 5-Rh, 6-Rh, 9-Rh, 12-Rh, 13-Rh, 14-Rh, 16-Rh, 22-Rh, 23-Rh, 27-Rh, 28-Rh, 30-Rh, 32-Rh, 12RH-NCN-1 and 28RH-NCN-1.

A method of determining if a compound binds to c-Myc, comprising: determining by fluorescent polarization if the presence of a first amount of one of a Myc protein or a portion of Myc protein that contains a c-Myc bHLH-ZIP dimerization/DNA binding domain in a solution containing a fluorescent polarizing compound de-polarizes light to a different degree as a solution containing a different amount, or none of the Myc protein or portion thereof, determining by x-ray crystallography if a compound binds to c-Myc bHLH-LZ; or determining by NMR spectroscopy if a compound binds to c-Myc bHLH-LZ. In one embodiment, as shown below, fluorescent polarization is used to determine if the compound binds to cMyc.

The starting compound for the current studies, (Z,E)-5-(4-ethylbenzylidene)-2-thioxothiazolidin-4-one (hereafter referred to as 10058-F4), is one of six first identified by our group (see, U.S. Pat. No. 7,026,343) and is structurally the simplest, being comprised of a six-member ethylbenzylidine ring and a five-member thioxothiazolidin-4-one, or rhodanine ring (Yin X, et al. Oncogene 2003; 22:6151-9 and FIG.

1A). The ability of 10058-F4 to target c-Myc-Max, to disrupt the heterodimer and/or to prevent its formation, and to abrogate various c-Myc-dependent functions has also been confirmed independently by several other groups (Kolly C, Suter M M, Muller E J. Proliferation, cell cycle exit, and onset of terminal differentiation in cultured keratinocytes: pre-programmed pathways in control of C-Myc and Notch1 prevail over extracellular calcium signals. J Invest Dermatol 2005; 124:1014-25; Gomez-Curet I, Perkins R S, Bennett R, Feidler K L, Dunn S P, Krueger L J. c-Myc inhibition negatively impacts lymphoma growth. J Pediatr Surg 2006; 41: 207-11; Mo H, Henriksson M. Identification of small molecules that induce apoptosis in a Myc-dependent manner and inhibit Myc-driven transformation. Proc Natl Acad Sci USA 2006; 103:6344-9 and Huang M J, Cheng Y C, Liu C R, Lin S, Liu H E. A small-molecule c-Myc inhibitor, 10058-F4, induces cell-cycle arrest, apoptosis, and myeloid differentiation of human acute myeloid leukemia. Exp Hematol. 2006; 34:1480-9). In combination, these properties have established 10058-F4 as an attractive starting point for the generation of analogs with improved efficacy.

Described herein are the consequences of altering both the six-member ethylbenzylidine ring and the five-member rhodanine ring of 10058-F4, either individually or in combination. Using several independent assays, a number of single ring derivatives have been identified as superior to 10058-F4. These results provide proof of principle that improved Myc-Max compounds can be obtained by a step-wise design approach. In addition, the finding that 10058-F4 and its active analogs bind specifically to monomeric c-Myc has implications for the future design of even more potent compounds.

EXAMPLES

Materials and Methods

In silico screening for Myc-Max compounds. In order to search for compounds related to 10058-F4 and which varied only in the six-member ring, we used the ChemFinder 7.0 software program (CambridgeSoft, Cambridge, Mass.). The 10058-F4 structure was then used to search the structure database file for the Chem Diversity library set (5040 total compounds; Chem Div, San Diego, Calif.) for related compounds. To search for 10058-F4 analogs which varied only in the five-member ring, we utilized a web-based search program (https://www.hit2lead.com/search_sc.asp) (Chembridge Corp., San Diego, Calif.) to screen a total of approximately 500,000 drug-like low molecular weight molecule compounds from the company's library with a substructure and similarity of >85%. A total of 141 compounds were identified by this method and 11 were chosen for more in-depth study.

Synthesis of 10058-F4 Analogs.

Preparation of RH and TZDD compounds. All reagents and solvents were >99% purity and were used as purchased (Sigma-Aldrich, St. Louis, Mo.; Fisher Scientific, Pittsburgh, Pa.). Rhodanine or 2,4-thiazolidinedione (3 mmol) and 0.69 g ammonium acetate were dissolved with heating in 4.5 ml glacial acetic acid. The carbonylic substrate (1.1 equivalents) was slowly added. The mixture was refluxed for 1 to 12 hr, cooled to room temperature and diluted with 50 ml water to precipitate the product. Compounds were characterized by $^1$H and $^{13}$C NMR. The reaction is stereoselective and only Z product is detectable by NMR. (Khodair A I. A convenient synthesis of 2-Arylidene-5H-thiazolo[2,3b]quinazoline-3,5 [2H]diones and their benzoquinazoline derivatives (2001) J of Heterocycl Chem. 2001; 39: 1153-60 and Neil S, Cutshall C, O'Day J, Prezhdo M. Rhodanine derivatives as inhibitors of JSP1. Bioorg Med Chem Letters 2005; 15:3374-9) Preparation of 1RH-S-Me. Rhodanine (10 mmol) was dissolved at room temperature in 25 ml followed by the addition of 0.5 M aqueous NaOH. CH3I (1.1 equivalents) was then added dropwise. The mixture was stirred at room temperature for 5.5 hr, extracted with three 15 ml portions of dichloromethane, and washed with water. The product was crystallized from methanol (Khodair A I. (2001) J of Heterocycl Chem. 2001; 39:1153-60 and Neil S, et al. Bioorg Med Chem Letters 2005; 15:3374-9).

Condensation of 1RH-S-Me with aldehydes. RH-S-Me (0.83 mmol) and 1.1 equivalents of aldehyde substrate were dissolved at room temperature in 2.5 ml anhydrous ethanol with triethylamine (115 µl). The mixture was stirred at room temperature until precipitate formed (15-90 min), then diluted with 20 ml water and acidified to pH 4-5 with 1N HCl. The precipitate was collected, washed with water and characterized as above (Husain M, Sarveshwar, I S. Synthesis and biodynamic activities of 5-(substituted benzylidene)-3-[p-(N,N-disubstituted carbamoyl)phenylaminomethyl]-4-oxothiazolidine-2-thiones Ind J Chem 1985; 24B:761-4).

Preparation of RH-NCN-1 compounds. Rhodanine (0.5 mmol) was dissolved in 2 ml hot ethanol. Formaldehyde (37% w/V in water, 1.2 equivalents) and piperidine (1.1 equivalents) were added. Product started precipitating in ~5 minutes. The mixture was than cooled and further stirred at room temperature for 2 hours. The precipitate was collected, washed with water and characterized as above (Ponzielli R, Katz S, Barsyte-Lovejoy D, Penn L Z. Cancer therapeutics: targeting the dark side of Myc. Eur J Cancer 2005; 41:2485-501).

Growth of Mammalian Cells.

HL60 human promyelocytic leukemia cells were grown in RPMI medium supplemented with 10% fetal calf serum, 100 U/ml penicillin G, and 100 µg/ml streptomycin (all from Mediatech, Inc., Herndon, Va.). Rat fibroblast lines were grown under similar conditions in Dulbecco's modified minimal essential medium. To determine the effects of Myc-Max compounds on HL60 cell growth, logarithmically growing cells (>90% viability) were resuspended in fresh medium. Four (4) ml (a total of 16,000 cells) were then seeded into 6-well plates in the presence of the indicated amount of Myc-Max compound. In all cases, 10058-F4 was included as a reference compound. Daily cell counts were performed manually in triplicate on a hemacytometer using trypan blue exclusion. Viabilities exceeded 85% throughout the course of the experiment.

Preparation of Cell Lysates and Co-Immunoprecipitation Experiments.

Nuclei from HL60 cells were prepared essentially as described previously (17). Briefly, approximately $4 \times 10^7$ washed nuclei were resuspended in 1 ml of ice cold buffer F, which contained 150 mM NaCl; 10 mM Tris-HCl, pH 7.1; 30 mM sodium pyrophosphate; 5 µM $ZnCl_2$; 0.1% Nonidet P-40; 0.1 mM $Na_3VO_4$; 1 mM PMSF; 2.5 U/ml each of pepstatin, leupeptin, and approtinin. All reagents were from Sigma-Aldrich (St. Louis, Mo.). The nuclear suspension was then disrupted with the microtip of a Branson sonifier at a setting of 5 for 60 sec, clarified by centrifugation (10,000 g for 10 min), and stored in 200 µl aliquots at −80° C. Aliquots were thawed only a single time for use in immunoprecipitations.

To perform immunoprecipitations, a total of 200 µl of the above-described nuclear extract was diluted in 0.5 ml of Buffer F along with the indicated final concentration of Myc- Max compound. Following incubation at 30° C. for 30 min, a polyclonal rabbit anti-Max antibody (Zhang H, Fan S, Prochownik E V. Distinct roles for MAX protein isoforms in proliferation and apoptosis. J Biol Chem 1997; 272; 17416-24) was added to a final dilution of 1:250 and the mixture was incubated with constant agitation at 4o C for additional 16 hr. 20 μl of protein G-agarose (Santa Cruz Biotechnology, Inc. Santa Cruz, Calif.) was then added for an additional 6 hr with agitation. The precipitate was collected by centrifugation, washed 3 times in Buffer F and boiled in SDS-PAGE lysis buffer. Western blotting of the lysate was then performed as previously described (Zhang H, et al. J Biol Chem 1997; 272; 17416-24). The upper portion of the blot was probed overnight with a 1:1000 dilution of a murine anti-c-Myc monoclonal antibody (mAb) 9E10 (Santa Cruz) and the lower portion was probed with a 1:1000 dilution of the H-2 murine mAb against Max (Santa Cruz, no. sc-8011). In both cases, the blots were then subsequently probed with a 1:10,000 dilution of HRP-conjugated goat anti-mouse IgG (Santa Cruz) and developed using an enhanced chemiluminescent kit (SuperSignal West Femto Maximum Sensitivity, Pierce, Rockland, Ill.) according to the directions of the supplier.

Expression and purification of recombinant $c$-$Myc_{353-439}$ and Max. The expression vector c-Myc/pET SKB3 [encoding the hexahistidine (His6)-tagged bHLH-LZ region of human Myc residues 353-439 with a GGCD extension at the C terminus] was kindly supplied by Dr. S. K. Nair (University of Illinois, Urbana-Champaign) and over-expressed in *E. coli* strain BL21DE3(plysS). $His_6$-tagged human Max isoforms, Max(L) (160 amino acids) and Max(S) (151 amino acids), both in the pQE-10 vector (Qiagen, Chatsworth, Calif.) (Zhang H, et al. J Biol Chem 1997; 272; 17416-24 and Prochownik E V, VanAntwerp M E. Differential patterns of DNA binding by myc and max proteins. Proc Natl Acad Sci USA 1993; 90:960-4), were over-expressed in *E. coli* strain M15(pRep4). Briefly, bacterial cultures were grown at 37° C. in LB to an $OD_{600}$≈0.8 and then induced with 0.5 mM IPTG for 5 hours. Cultures were harvested and lysed in a buffer containing: 8 M urea; 100 mM $NaH_2PO_4$; 10 mM Tris; pH 8.0. Proteins were purified on an NTA-Ni column with a pH gradient elution. Max proteins were further purified by reversed-phase HPLC. The $His_6$ tag of $c$-$Myc_{353-439}$ was cleaved using TEV protease (previously expressed in a pET24 vector [from S. K. Nair] and purified on NTA-Ni-agarose under native conditions). The final c-Myc bHLH-LZ product was then further purified by HPLC and lyophilized.

Electrophoretic mobility shift Assays (EMSAs). Experiments were performed on 8% polyacrylamide:bis-acrylamide (80:1) gels in 0.5×TBE. Binding reactions were prepared in a buffer consisting of 1×PBS (pH 7.3); 1 mM EDTA; 0.1% NP40; 5% glycerol; 1 mM dithiothreitol; and 0.4 mg/mL BSA. A 22 base-pair E-box-containing double-stranded DNA oligonucleotide labeled on one strand with hexachlorofluoresceine (HEX) consisted of the following sequence:

5'-HEX-CACCCGGT*CACGT*GGCCTACAC-3'    (SEQ ID NO: 1)

and was synthesized by Integrated DNA Technologies Inc (Coralville, Iowa). The oligonucleotide was used at 10 nM concentration in all reactions, which also contained 60 nM each of purified c-Myc bHLH-LZ, Max(S), and the indicated amount of each compound. Proteins were first incubated for 90 min at 25° C., followed by addition of the oligonucleotide and an additional 15 minutes incubation before loading on a running gel. Gels were run at 20° C. and scanned on a BioRad FX molecular imager (BioRad, Hercules, Calif.). Data were analyzed with BioRad Quantity One software.

Fluorescence polarization assays. Samples of inhibitor at 25 μM concentration, in the absence and presence of an equimolar concentration of purified $c$-$Myc_{353-439}$ peptide, were prepared in 1×PBS buffer (pH 7.4); 1 mM DTT; 5% DMSO. The samples were analyzed in a Photon Technology International QuantaMaster fluorimeter (Birmingham, N.J.) equipped with polymer sheet polarizers at an excitation wavelength of 380 nm and an emission wavelength of 468 nm. Alternative settings (ex: 470 nm; em: 600 nm), were employed for the compounds 7RH and 8RH, which have longer wavelength absorption and emission spectra. Each sample was analyzed in triplicate at 25° C. with sample specific G-factor determination. Titration experiments were performed with the same instrumental settings, temperature, and buffer conditions upon two-fold serial dilution of equimolar mixtures of inhibitor and $c$-$Myc_{353-439}$. Reported data represent the average of three to five independent experiments. Data were fit to a quadratic equation derived from the thermodynamic expression of binding equilibrium:

$$\frac{[\text{complex}]}{[C]_0} = \frac{2 + K_{obs}/[C]_0 - \sqrt{(-2 - K_{obs}/[C]_0)^2 - 4}}{2}, \quad \text{Eq. 1}$$

where $[C]_0$ represents the total concentration of inhibitor and of $c$-$Myc_{353-439}$. The value of Kobs was determined from the experimental polarization data by fitting to Eq. 2 using KaleidaGraph (Synergy Software, Reading, Pa.) where $pol_0$ is the polarization in the absence of binding and Δpol is the total change in polarization (Park S-H, Raines R T. Fluorescence polarization assay to quantify protein-protein interactions, Methods Mol Biol 2004; 261:161-165 (2004)).

$$\text{polarization} = pol_0 + \Delta pol\left(\frac{[\text{complex}]}{[C]_0}\right). \quad \text{Eq. 2}$$

Results

Figure 9:
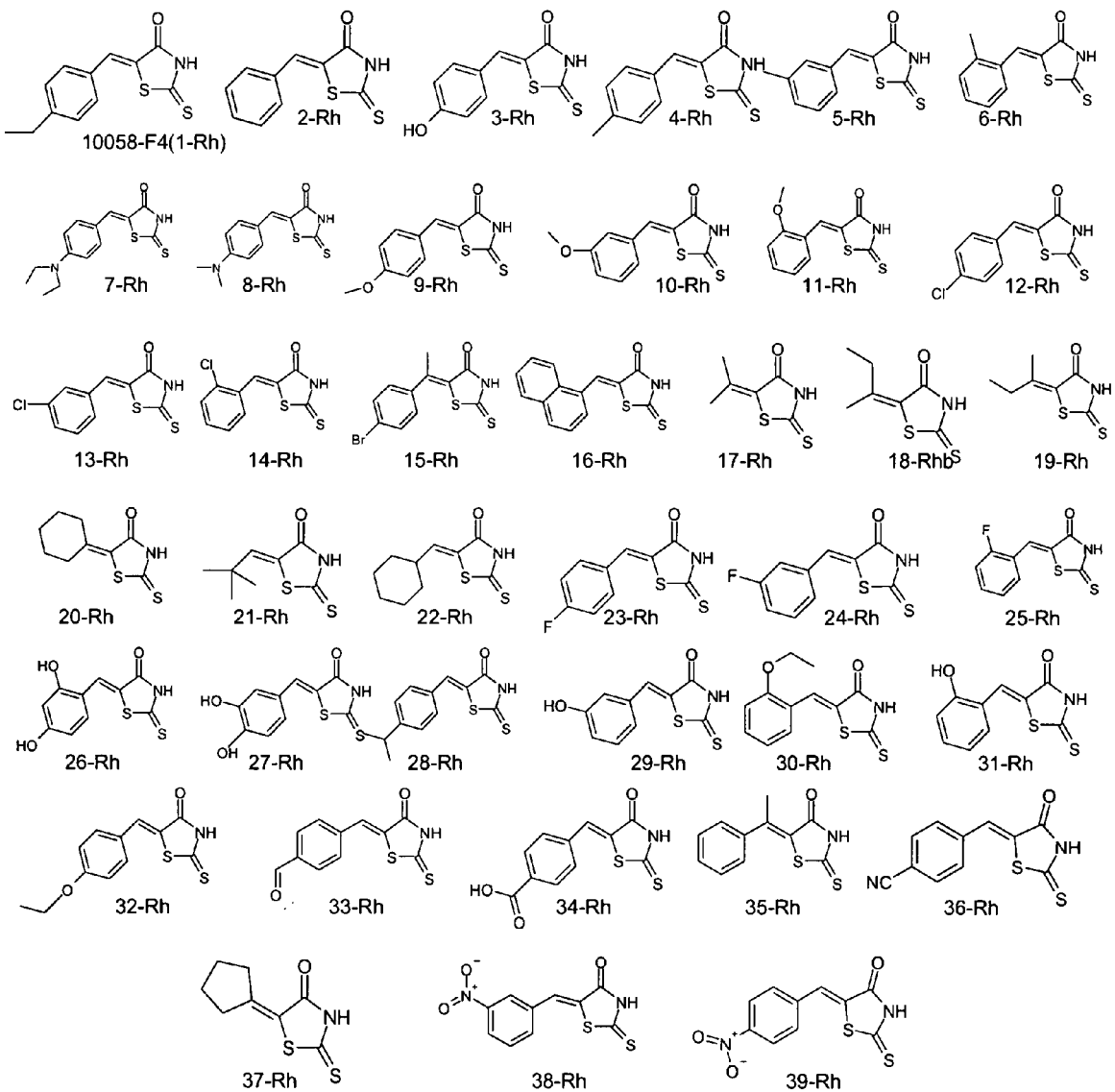

Modification of the six-member ring of 10058-F4. To identify candidate 10058-F4 analogs with improved efficacy, an initial in silico screen of the 5040 member low molecular weight ChemDiversity library was conducted for structures that shared the same five-member rhodanine ring as the parental compound but that contained variations of the six-member ring. This search yielded a total of ten so-called "second generation" compounds. A library of 38 additional compounds was also synthesized. The structures of all of these are depicted in FIG. 9.

Each compound was initially tested for its ability to inhibit the growth of the HL60 human promyelocytic leukemia cell line, which expresses high levels of c-Myc as a result of gene amplification (Park S—H, et al. Methods Mol Biol 2004; 261:161-165 (2004)). Because this assay is biologically based, it serves as an easy, rapid, and accurate means of eliminating pharmacologically inactive agents. In each case, 10058-F4 was included in parallel assays to permit direct and immediate comparison with all test compounds. From this initial screen, we identified several analogs that were at least as potent as 10058-F4. FIG. 1A shows the structures of the four most active analogs, their dose-response profiles, and their $IC_{50}$'s. From these results, it can be seen that one compound, namely 27RH was approximately twice as potent as 10058-F4 (ID$_{50}$ 23 μM vs. 51 μM) whereas a second compound, 28RH was only marginally better (ID$_{50}$ 36 μM). It was concluded that alterations of the six-member ring of the 10058-F4 index compound lead to modest, but significant improvements of in vivo activity. The frequency with which such analogs are identified is also quite low.

Figure 2A:
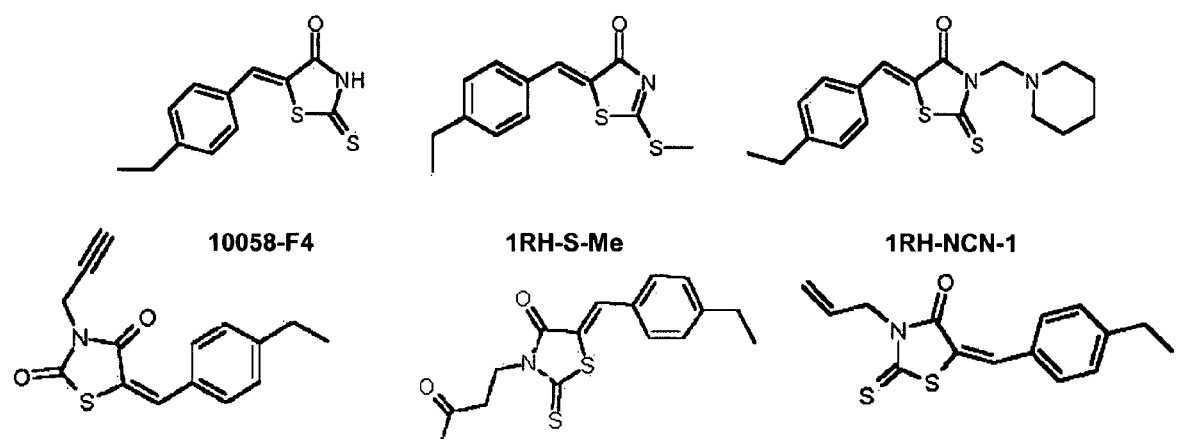
FIG. 2A shows structures of the most active five-member ring. All compounds bearing the "1RH" prefix contain a six-member ring identical to that in 10058F4.
Figure 10:
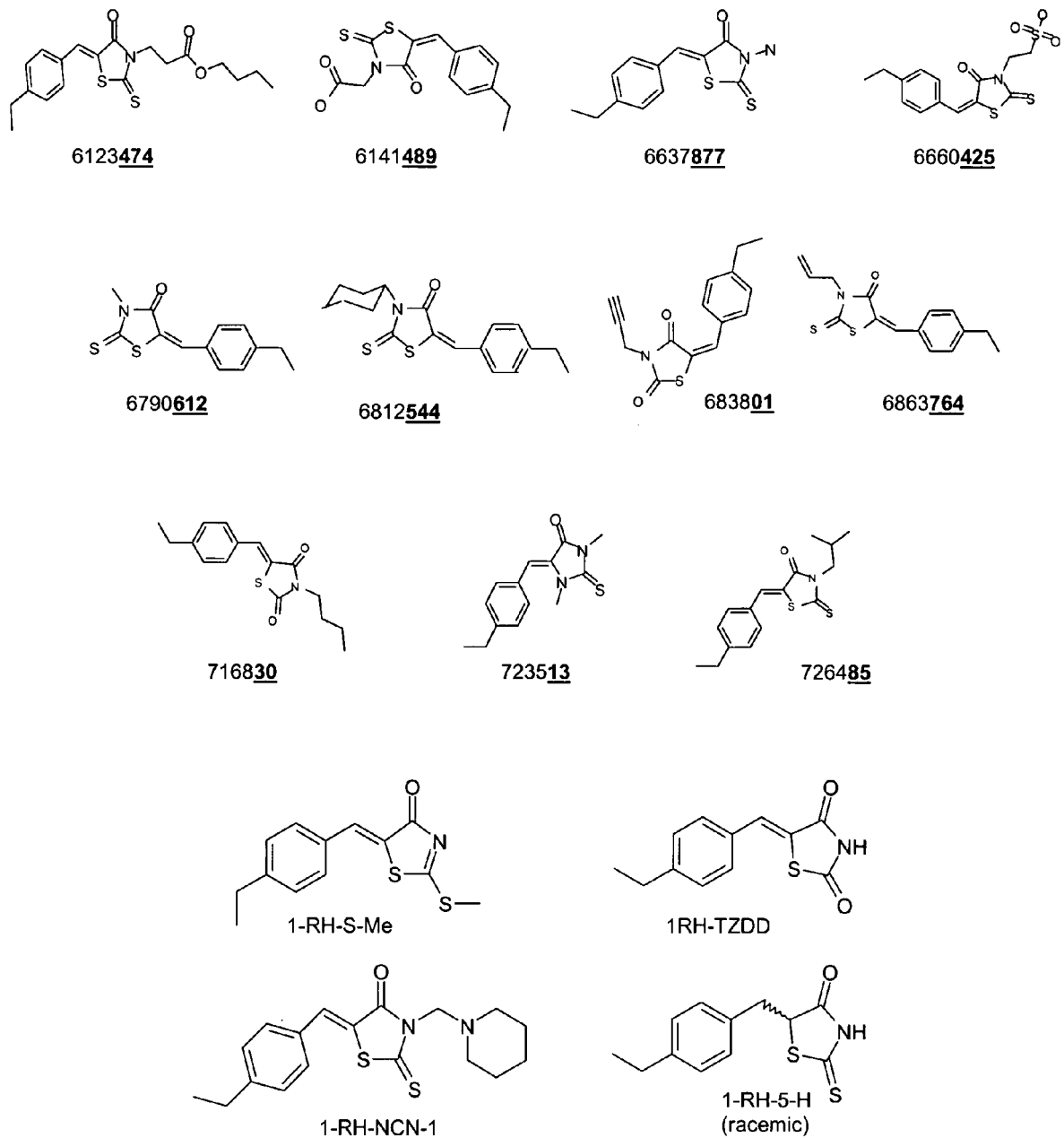
FIG. 10 provides structures of five-member ring "second generation" analogs of index compound 10058-F4 (1RH). An in silico screen, similar to that described in connection with FIGS. 8 and 9, was performed on the Chembridge set of 500,000 low molecular weight compounds and identified a total of 11 novel 5-member ring analogs of 10058-F4. We also synthesized an additional 4 compounds (those designated with "RH").

Modification of the five-member rhodanine ring of 10058-F4. The foregoing studies established that the structure of 10058-F4's six-member ring could be altered so as to produce analogs with modestly improved efficacy. In order to explore further the consequences of other structural alterations, we performed an additional in silico screen of a 500,000-member low molecular weight compound library (Chembridge Inc., San Diego, Calif.) for 10058-F4 analogs whose only modification was in the five-member rhodanine ring. A total of eleven compounds were identified in this way and four additional ones were synthesized. The structures of each of these compounds are depicted in FIG. 10, and those of the five most active compounds are depicted in FIG. 2A.

Figure 2B:
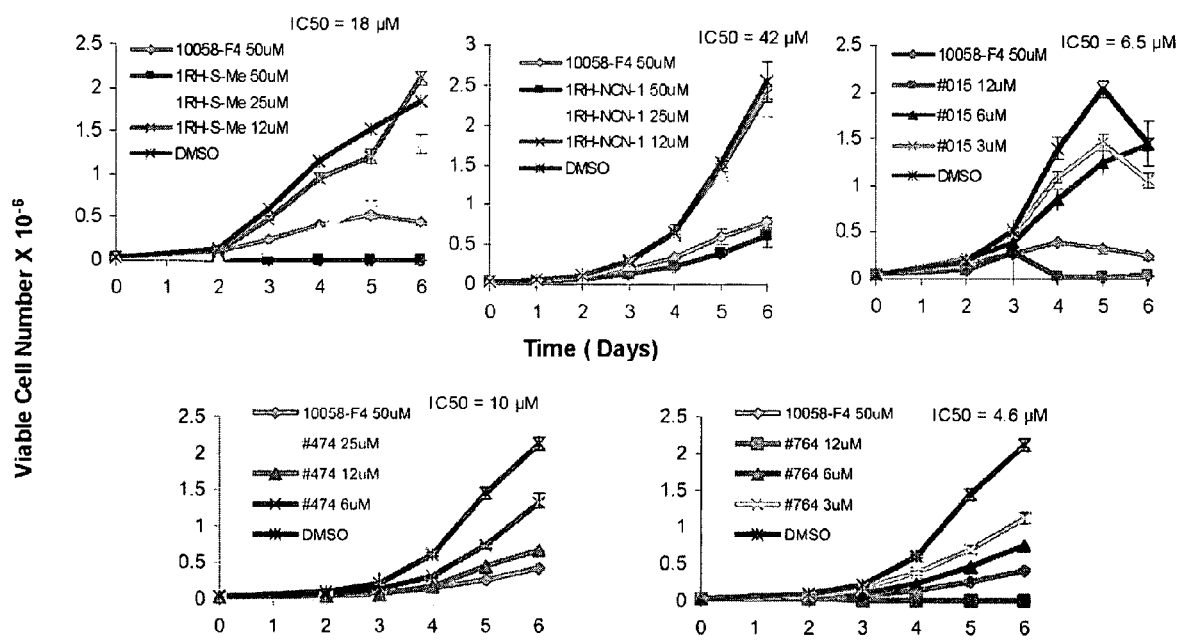
FIG. 2B provides dose-response profiles of each of the compounds on HL60 cell growth.

Each analog was again tested in HL60 cells as described above. Although numerous active compounds were identified, only four (1RH-S-Me, #015, #474, and #764) were significantly more active than 10058-F4 with ID$_{50}$'s ranging from 4.6-18 μM (FIG. 2B).

Figure 1B:
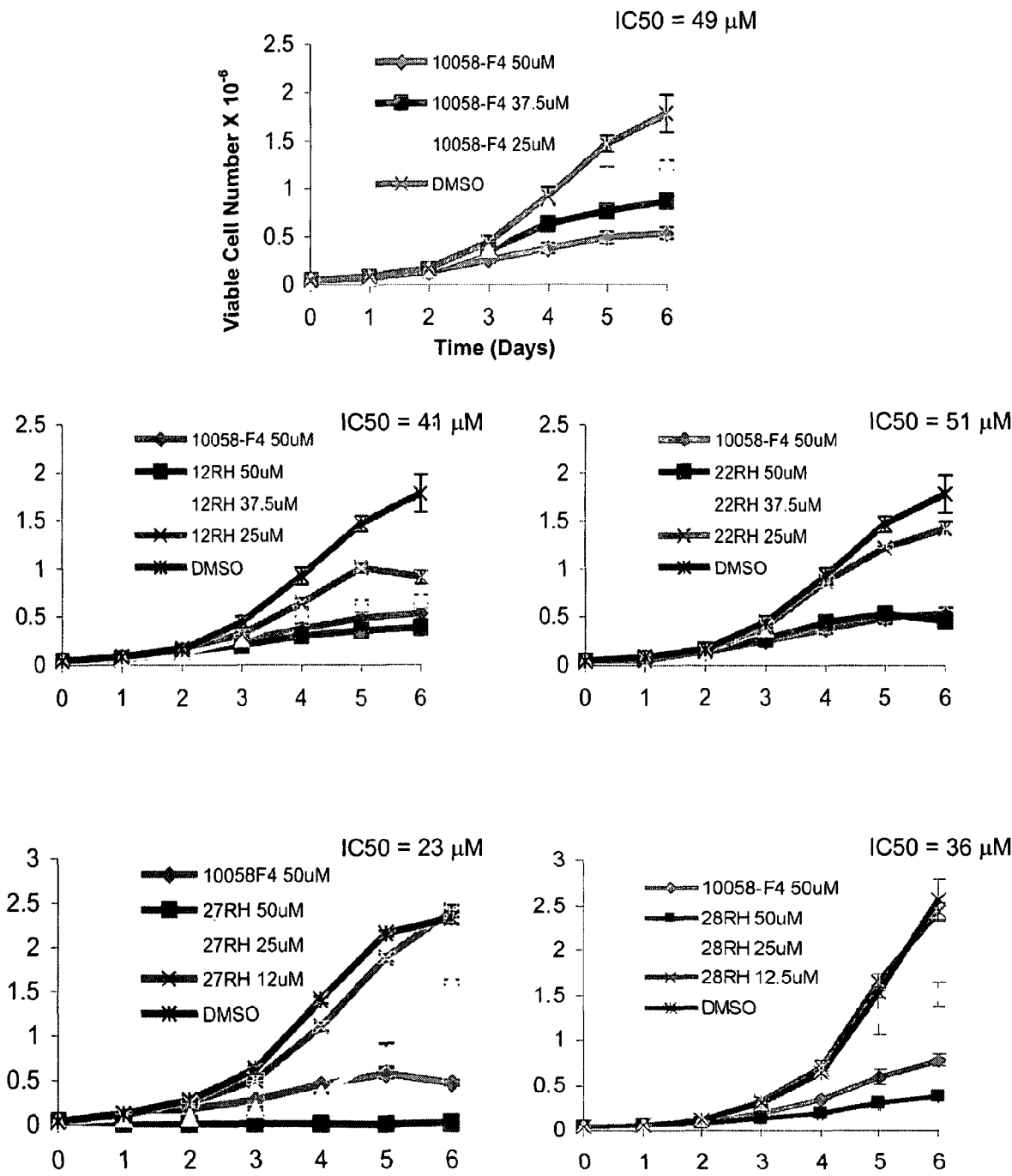
FIG. 1B shows dose-response profiles of each of the compounds on HL60 cell growth. Note that all structures shown herein are drawn in their Z-isoform and some bonds have been standardized. IC50's here, as well as below for in FIGS. 2 and 3, were calculated based upon dose-response profiles on day 5 following the addition of each compound.
Figure 3A:
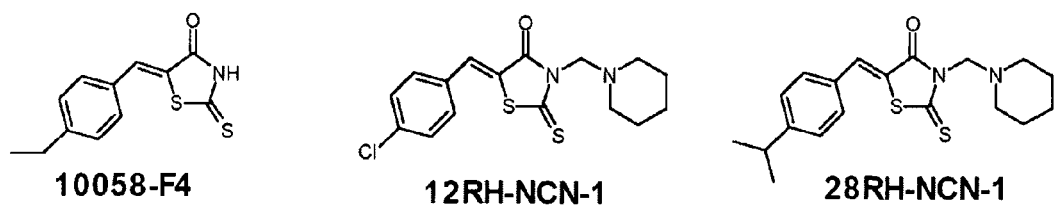
FIG. 3A shows structures of hybrid compounds containing "optimized" six- and five-member rings derived from select compounds shown in FIGS. 1A and 2A.
Figure 3B:
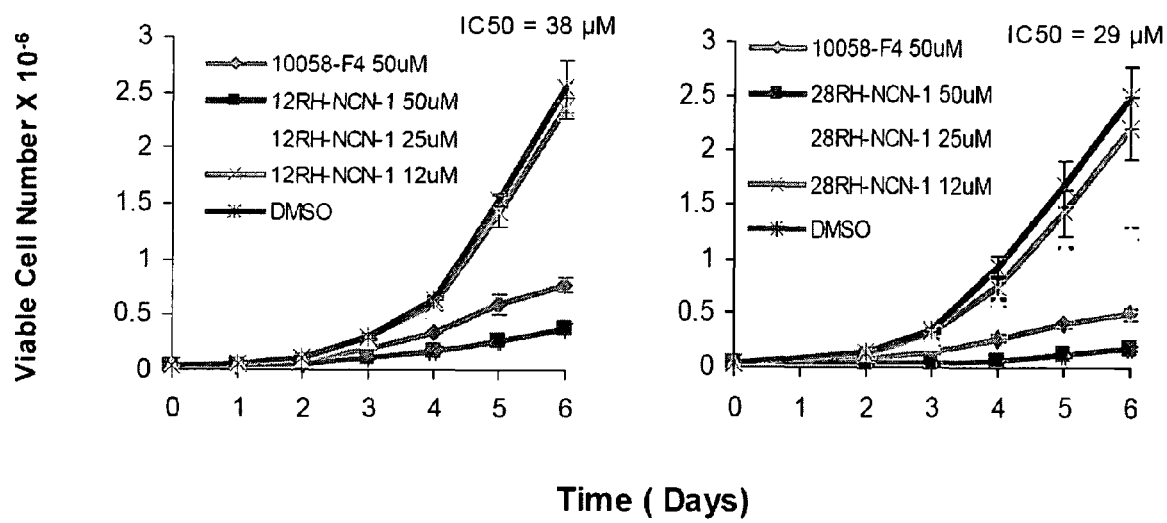
FIG. 3B shows the results of HL60 proliferation assays performed with the above compounds.
Figure 11:
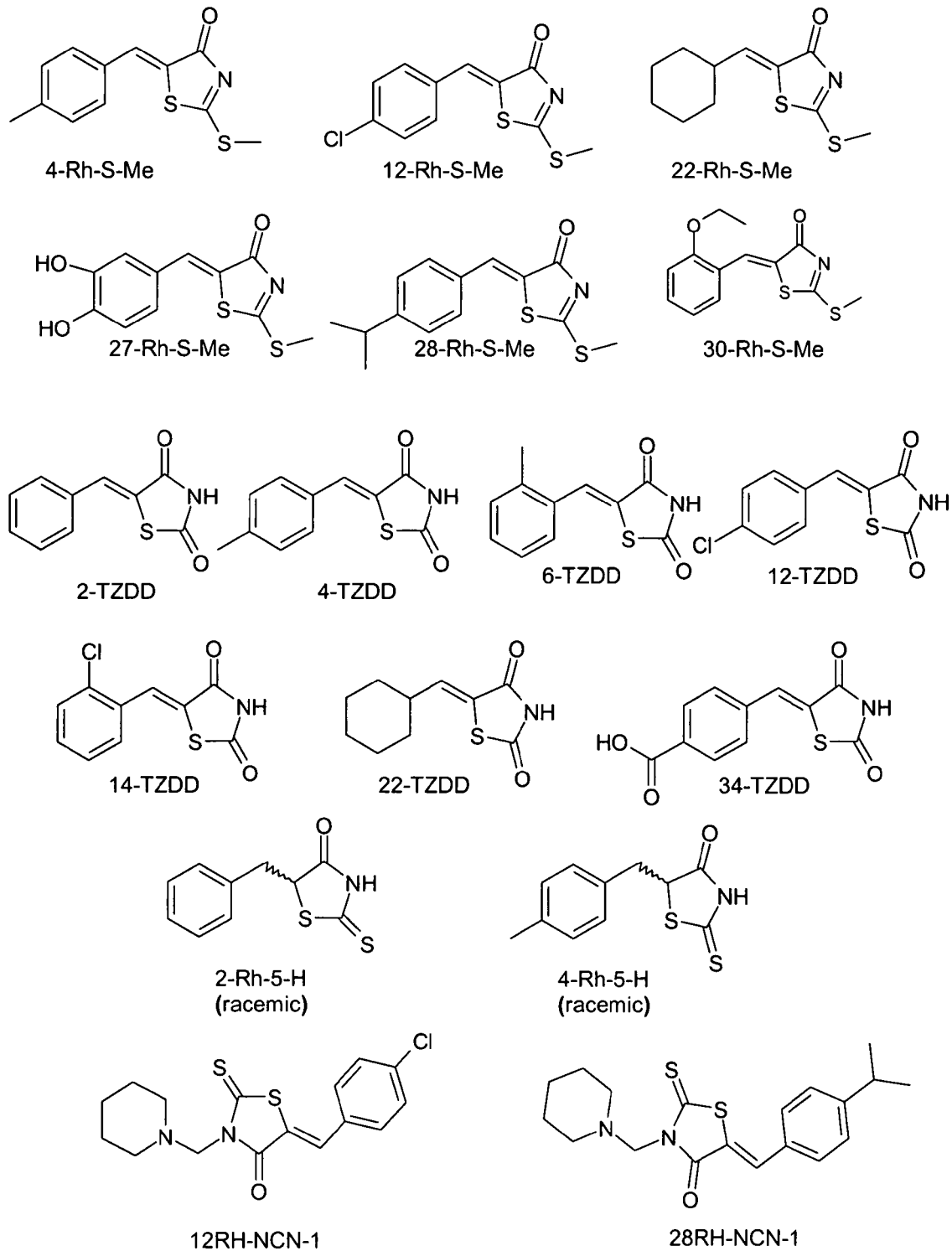
FIG. 11 provides structures of "third generation" compounds containing optimized 5- and 6-member rings.

Combined modification of the five- and six-member rings of 10058-F4 fail to provide additive potency. The foregoing results indicated that certain modifications of 10058-F4's component rings lead to enhanced activity. In order to determine whether the idealized ring structures from these "second generation" compounds could be combined additively so as to further improve their activities, we next synthesized and tested a group of 17 "third generation" compounds containing select combinations of optimized five- and six-member rings (FIG. 11 and FIG. 3A). The choice of each starting ring structure was based on a combination of the results of screens depicted in FIGS. 1 and 2, preliminary evaluation in electrophoretic mobility shift assays (not shown), and the ease of synthesis and yield of the final compound. As shown in FIG. 3B, only two compounds, namely 12RH-NCN-1 and 28RH-NCN-1, demonstrated activities comparable to that of 10058-F4 in HL60 cells. Of particular significance was that each of these was either inferior to or only marginally better than each of its second-generation predecessors. From these and the foregoing studies, we conclude that the greatest improvements in efficacy resulted from select changes in only the rhodanine ring of 10058-F4.

Figure 4A:
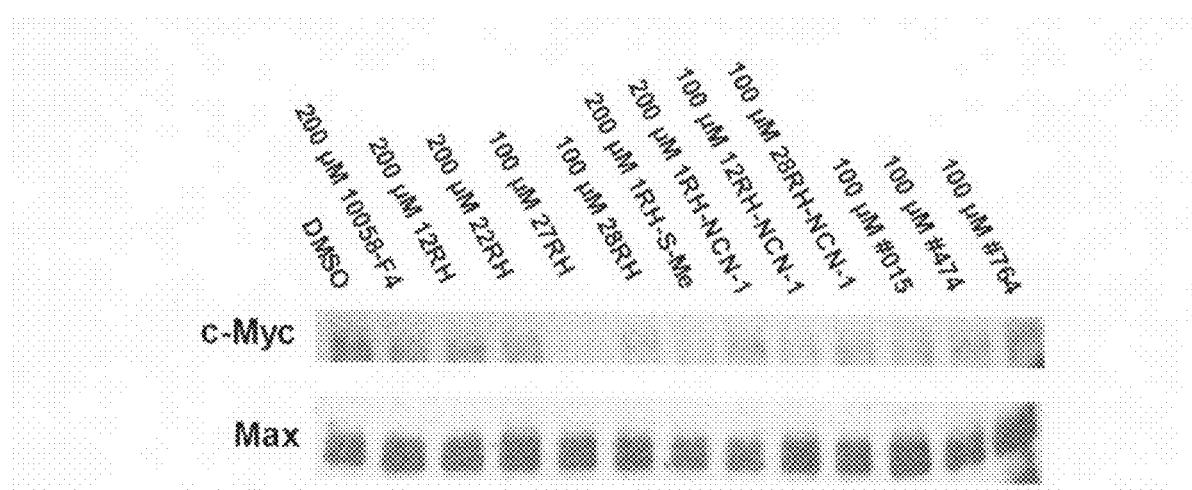
FIG. 4A shows co-immunoprecipitation of c-Myc and Max from HL60 nuclear extracts. Equivalent amounts of nuclear extracts were incubated with the indicated concentrations of the compounds depicted in FIGS. 1-3. Following precipitation of the complexes with an anti-Max antibody, the total amount of associated c-Myc was detected by immunoblotting (top panel). As a control, the lower portion of the blot was probed with an anti-Max antibody (bottom panel).

10058-F4 analogs interfere directly with c-Myc-Max heterodimerization and DNA binding. The above studies were designed to serve as rapid, biologically-based screens for Myc-Max compounds with the greatest in vivo potencies. However, they did not necessarily establish that the observed effects were due specifically to the disruption of c-Myc-Max complexes, as had been previously shown for the parent 10058-F4 compound. To address this, the effect of each compound on c-Myc-Max association was determined in vitro by two different methods. In the first, nuclear extracts from HL60 cells were incubated with each compound and a co-immunoprecipitation (co-IP) was performed with an anti-Max antibody (Zhang H, et al. J Biol Chem 1997; 272; 17416-24). The total amount of co-precipitating c-Myc protein was then assessed by immunoblotting. As a co-IP control, the same blot was also probed for Max. As shown in FIG. 4A, 10058-F4, as well as all tested analogs, promoted the dissociation of c-Myc from Max in this assay. In general, good, albeit inexact, correlations between this assay and in vivo assays were observed. Control experiments further established that none of the compounds affected the absolute levels of either c-Myc or Max (FIG. 4A and data not shown).

Figure 4B:
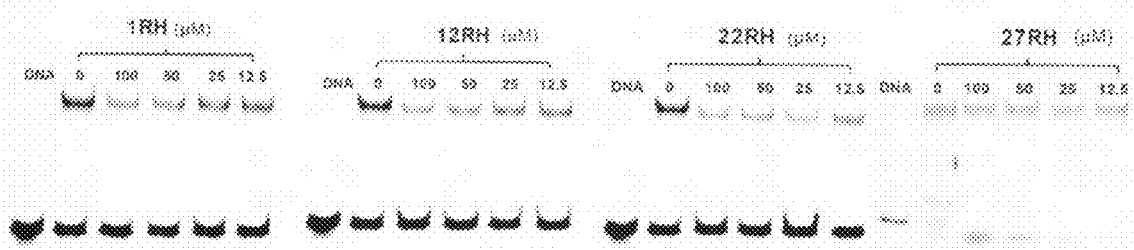
FIGS. 4B, 4C and 4D show EMSAs results. Recombinant c-Myc$_{353-439}$ (which encodes the complete bHLH-ZIP dimerization domain) and full-length Max(S) were purified to homogeneity from *E. coli* and used at a final concentration of 60 nM in the presence of the indicated concentration of compound. Control experiments demonstrated that none of the compounds significantly affected DNA binding by Max(L) homodimers (not shown).
Figure 4C:
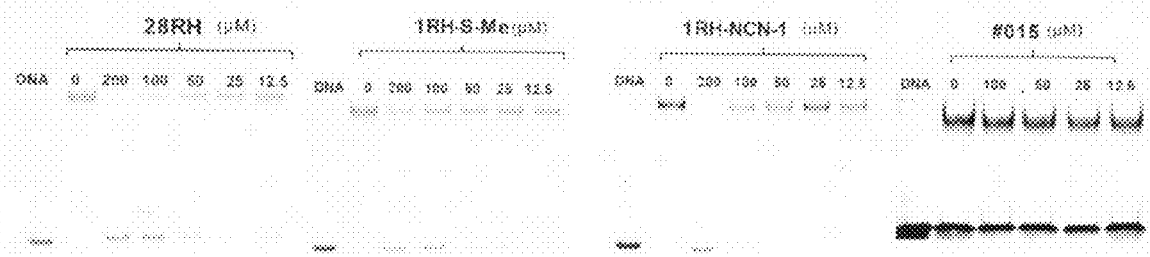
Figure 4D:
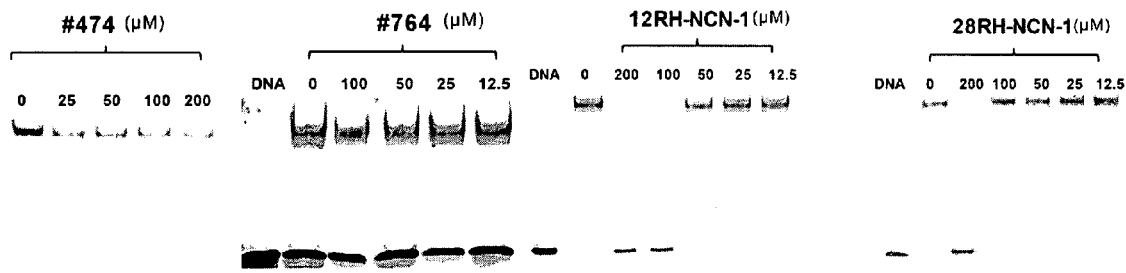

The second method used to gauge the effects of 10058-F4 and its analogs on c-Myc-Max complexes relied on the use of a simple, three component electrophoretic mobility shift assay (EMSA). For this purpose, a recombinant c-Myc peptide, which encompasses the bHLH-LZ domain (c-$Myc_{353-439}$), together with the full-length His$_6$-tagged 151 amino acid isoform of Max [designated Max(S)] (Zhang H, et al. J Biol Chem 1997; 272; 17416-24 and Prochownik E V, et al. Proc Natl Acad Sci USA 1993; 90:960-4) were incubated in increasing concentrations of each relevant compound. The ability of the resultant heterodimer to bind a double-stranded target oligonucleotide containing a consensus E-box motif was then assessed by PAGE. In order to simplify interpretation of the assay, we purposely utilized Max(S) since, unlike Max(L), it is unable to bind DNA as a homodimer at the concentrations used here (Zhang H, et al. J Biol Chem 1997; 272; 17416-24 and Prochownik E V, et al. Proc Natl Acad Sci USA 1993; 90:960-4). Because c-Myc is unable to form homodimers, any observed shifted band must be indicative of DNA binding by the c-Myc-Max(S) heterodimer (Zhang H, et al. J Biol Chem 1997; 272; 17416-24 and Prochownik E V, et al. Proc Natl Acad Sci USA 1993; 90:960-4). As seen in FIGS. 4B, 4C and 4D, the expected DNA binding was readily observable in the absence of any added compound, whereas the addition of 10058-F4 and all tested analogs resulted in a dose-dependent, although variable, inhibition, with compounds 28RH and 12RH-NCN1 being among the most effective. In control experiments (not shown), it is shown that DNA binding by the 161 amino acid Max isoform [Max(L)] was unaffected by these compounds. As in the case of the co-IP experiments, these studies establish a correlation between the in vivo efficacy of certain of these compounds and their ability to affect c-Myc-Max association and DNA binding in vitro. In addition, they are consistent with data obtained in HL60 cells that modification of the 10058-F4 parental backbone can enhance in vivo efficacy.

Figure 5:
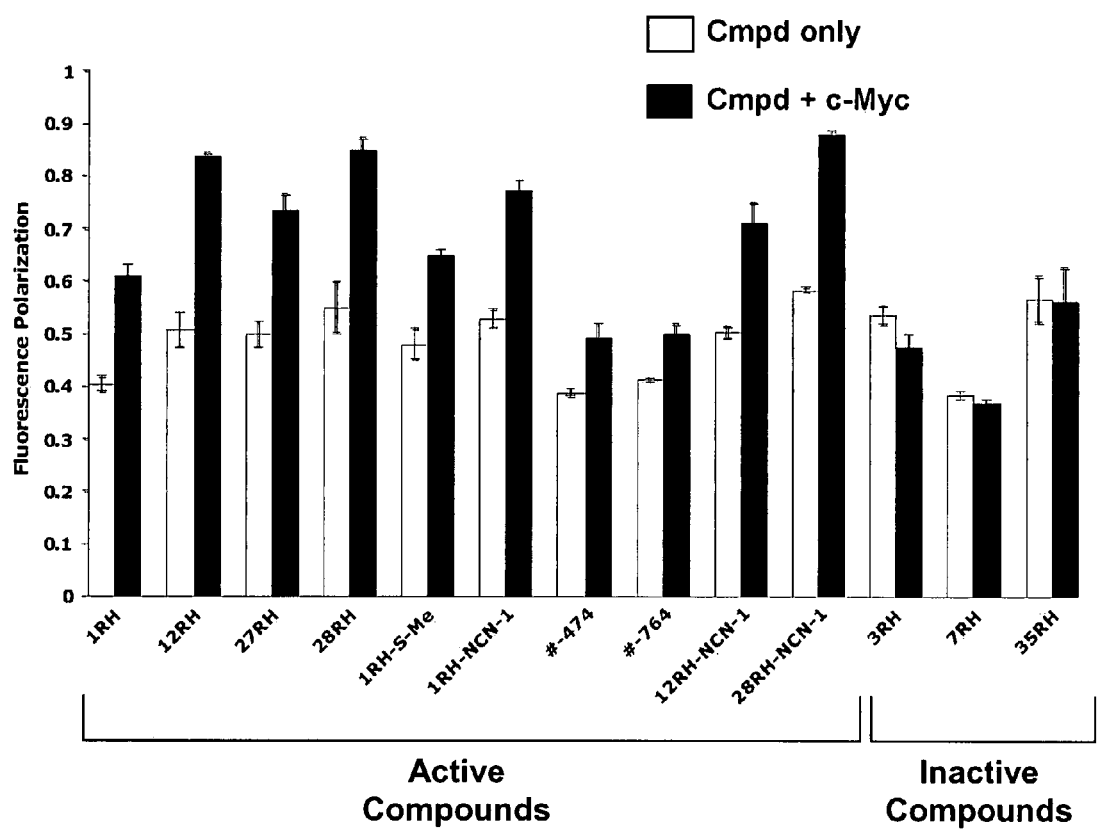
FIG. 5 provides the results of fluorescence polarization assays. Each of the indicated compounds was assayed in triplicate at a final concentration of 25 μM in the presence or absence of 25 μM recombinant c-Myc$_{353-439}$. Excitation and emission maxima were 380 nM and 468 nM, respectively.

10058-F4 and its analogs bind directly to c-Myc. Previous studies with 10058-F4 and other structurally unrelated index compounds had not specifically addressed the question of whether their binding required intact c-Myc-Max heterodimers or could occur on monomeric forms of the proteins. In order to address this, we took advantage of the fact that 10058-F4, and most of its analogs, are fluorescent and can depolarize an incident beam of light. Because the degree to which this occurs is partly a function of the molecule's rate of tumbling in solution, binding to either c-Myc or Max should result in a loss of fluorescence depolarization. As seen in FIG. 5, this occurred in the case of 10058-F4 and all active analogs upon the addition of c-Myc$_{353-439}$. In contrast, inactive 10058-F4 analogs failed to bind (FIG. 5 and unpublished results). Similar experiments performed with recombinant Max(S) protein failed to provide evidence of binding of any of the compounds (not shown). Together with our other findings, these results support the idea that the activity of 10058-F4 and its analogs arise from their ability to bind directly to the c-Myc bHLH-LZ monomer.

The binding affinities for selected active compounds were determined by titrating them with c-Myc$_{353-439}$ and following the change in polarization of their intrinsic fluorescence. When unbound, the inhibitors exhibit low fluorescence polarization. When excited with polarized light, they emit substantially depolarized light due to their rotation during the fluorescence lifetime. When the compounds are bound to c-Myc$_{353-439}$, the polarization increases due to slower tumbling and this change can be used to calculate an observed binding constant. The affinity of parental 10058-F4 for c-Myc$_{353-439}$ determined this way was 2.3±0.7 µM (FIGS. 6A-6D). In the initial set of modifications to the aromatic moiety, 12RH was found to have an affinity similar to 10058-F4 while the dihydroxy derivative 27RH was several fold worse in this direct binding assay. In this group, only 28RH (1.0±0.4 µM) was found to bind better than 10058-F4 (22RH is nonfluorescent and could not be assayed). With the exception of the linear ester derivative (#474), modification of the rhodanine ring lead to an approximately two-fold decreases in c-Myc$_{353-439}$ affinity. Combining modifications that either did not change binding (12RH) or reduced binding (1RH-NCN1) relative to 10058-F4 actually led to the tightest binding compound, 12-RH-NCN1, which had an affinity of 0.6+/−0.2 µM. The non-additive nature of the modifications may be a consequence of the flexibility of monomeric, predominately unstructured c-Myc$_{353-439}$, which may adopt somewhat different conformations to bind modified compounds. A compound with modifications at both sites may be binding a c-Myc conformation different from that which binds compounds with only singly modified rings.

Figure 7:
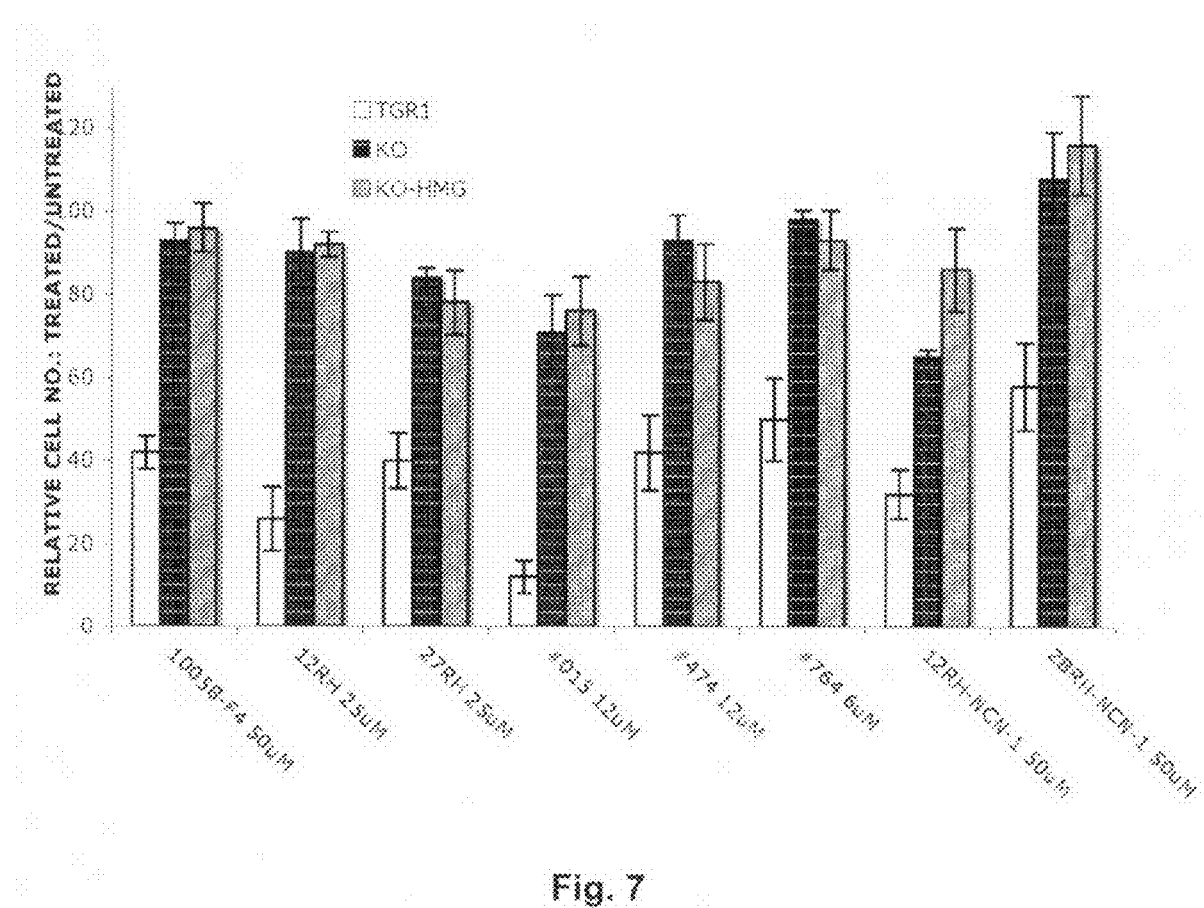
FIG. 7 illustrates the specificity of Myc-Max compounds for c-Myc-expressing cell. The related rat fibroblast cell lines TGR1, KO, and KO-HMG (Leglise M C, Dent G A, Ayscue L H, Ross D W. Leukemic cell maturation: phenotypic variability and oncogene expression in HL60 cells: a review. Blood Cells 198813:319-37 and Mateyak M K, Obaya A J, Adachi S, Sedivy J M. Phenotypes of c-Myc-deficient rat fibroblasts isolated by targeted homologous recombination. Cell Growth Differ. 1997; 8:1039-48) were seeded at 5×104 cells/well into 6-well plates and allowed to achieve logarithmic growth (1-2 days). Fresh medium containing the indicated concentrations of Myc-Max compounds was then added. TGR1 and KO-HMG cells were then further incubated for an additional 3-4 days, a point at which cells without compounds had achieved 70-90% confluency. KO cells were allowed to grow for an additional 4-5 days in order to compensate for their overall slower rate of proliferation, with compound-containing medium being changed every 2-3 days. Cells were then trypsinized and viable cell numbers determined in triplicate cultures using trypan blue dye exclusion. All cell numbers are normalized to identical sets of control, untreated cells cultured in parallel.
Figure 8:
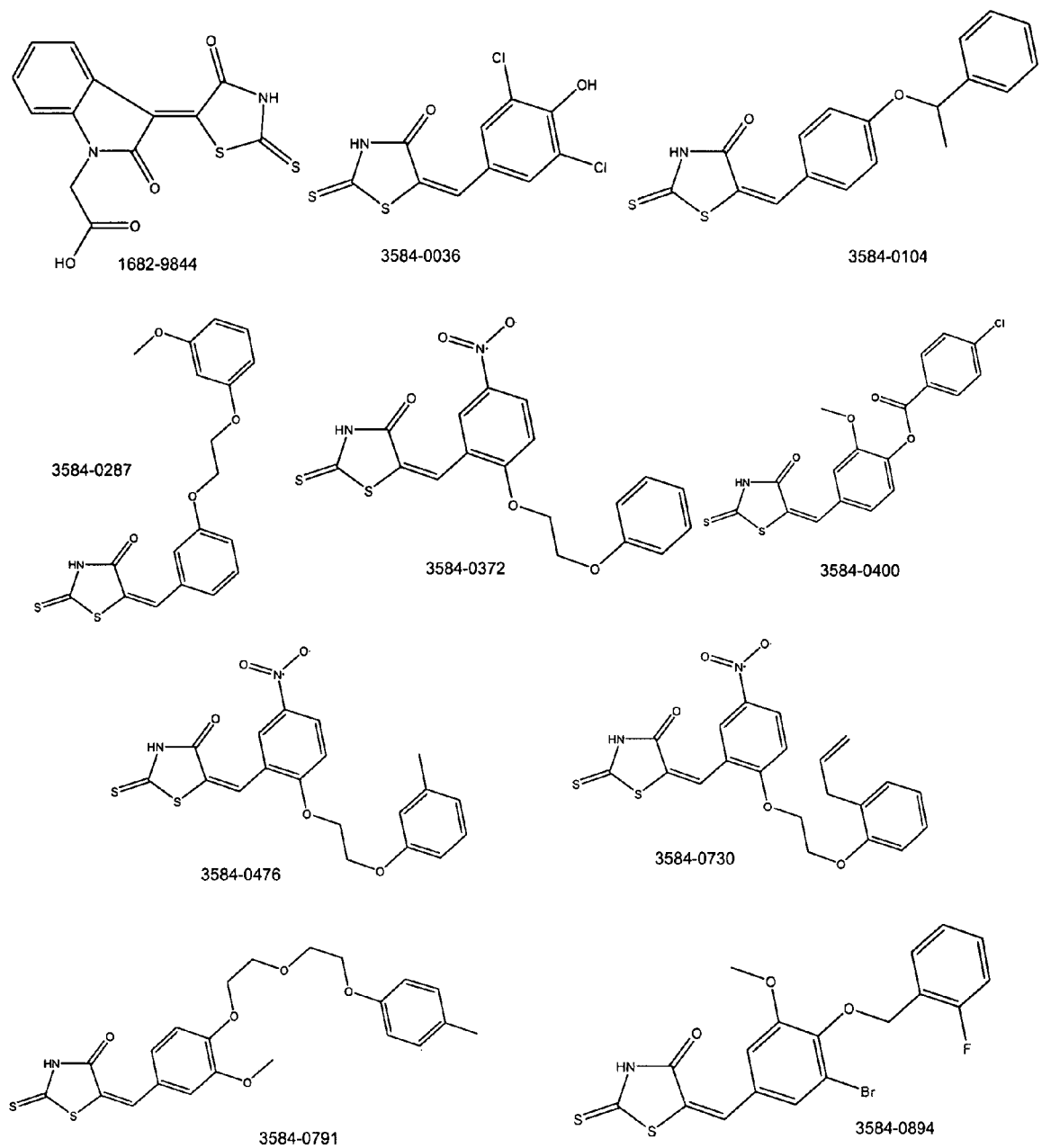
FIGS. 8 and 9 show structures of six-member ring "second generation" analogs of index compound 10058-F4 (1RH). A total of 5040 compounds, comprising the ChemDiversity library, were screened using the ChemFinder 7.0 program as described in Materials and Methods. This screen yielded a total of 10 compounds (FIG. 8), which are depicted with their ChemDiversity identification numbers. In addition, we synthesized our own small 38 member library of six-member ring variants (2RH-39RH, FIG. 9). Note that in some instances, the parental 10058-F4 compound is designated as "1RH".

10058-F4 analogs show selectivity for c-Myc expressing cells. Our initial mammalian cell-based screening assays for Myc-Max compound efficacy (FIGS. 1-3) were performed in HL60 cells because of their high level expression of c-Myc (Leglise M C, Dent G A, Ayscue L H, Ross D W. Leukemic cell maturation: phenotypic variability and oncogene expression in HL60 cells: a review. Blood Cells 1988 13:319-37). It was reasoned that those compounds capable of inhibiting HL60 growth should also be effective against other tumor lines, which generally express lower levels of c-Myc. However, inhibition of HL60 growth per se does not prove in vivo specificity, even though in vitro assays were consistent with such a conclusion. In order to test this, several of the most potent compounds were evaluated in three related Rat fibroblast cell lines. The first, HO16.4C, is a homozygous c-Myc-/-"knockout" cell line (KO cells) derived by homologous recombination from the second, parental cell line, TGR1 (Mateyak M K, Obaya A J, Adachi S, Sedivy J M. Phenotypes of c-Myc-deficient rat fibroblasts isolated by targeted homologous recombination. Cell Growth Differ. 1997; 8:1039-48). The third cell line, KO-HMG, was derived from HO16.4C cells and ectopically expresses HMGA1b, a member of the high mobility group of architectural transcription factors. We have previously shown that KO-HMG cells grow more rapidly than TGR1 cells despite their lack of c-Myc expression (Rothermund K, Rogulski K, Fernandes E, Whiting A, Sedivy J, Pu L, et al. C-Myc-independent restoration of multiple phenotypes by two C-Myc target genes with overlapping functions. Cancer Res. 2005; 65:2097-07). As seen in FIG. 7, TGR1 cells showed significant growth inhibition at the compound concentrations tested. In contrast, both KO cells and KO-HMG cells were significantly more resistant to identical concentrations of the compounds. Because KO-HMG cells divide at least as rapidly as the TGR cell line from which they are derived (Rothermund K, et al. Cancer Res. 2005; 65:2097-07), these differences cannot be attributed to any disparities in growth rates of the cell lines. From these studies, we conclude that, like the parental compound, the ability of 10058-F4 analogs to inhibit the growth of mammalian cells is c-Myc-dependent.

Resolution of the pathways leading to malignant transformation and progression has allowed for the rational design of chemotherapeutic agents with improved specificities and therapeutic indices. The as yet early successes with such "targeted therapies" make it highly likely that similar strategies will continue to be used well into the future. Among the most commonly de-regulated oncogenes in human cancer is CMYC, a general bHLH-LZ transcription factor that regulates hundreds of downstream target genes (Nesbit C E, et al. Oncogene 1999; 18: 3004-16; Prochownik E V. Expert Rev Anticancer Ther 2004; 4: 289-302; Dang C V. c-Myc target genes involved in cell growth, apoptosis, and metabolism. Mol Cell Biol 1999; 19:1-11; Cole M D, et al. Curr Top Microbiol Immunol 2006; 302:33-50; Kleine-Kohlbrecher D, et al. Curr Top Microbiol Immunol 2006; 302:51-62). As a result, the c-Myc oncoprotein, in addition to promoting transformation, exerts control over such basic cellular properties as proliferation, growth, metabolism, and differentiation. A number of model systems have clearly demonstrated the ongoing need for c-Myc in maintaining tumor growth and viability, thus underscoring its attractiveness as a therapeutic target (Felsher D W. Reversibility of oncogene-induced cancer. Curr Opin Genet Dev 2004; 14:37-42 and Flores I, Murphy D J, Swigart L B, Knies U, Evan G I. Defining the temporal requirements for Myc in the progression and maintenance of skin neoplasia. Oncogene 2004; 23:5923-30).

Here, it is shown that low molecular weight compounds or short helix-1-related bHLH-LZ peptido-mimetics can prevent or disrupt c-Myc-Max heterodimer formation or its binding to E-box motifs (see also, Berg T, et al. Proc Natl Acad Sci USA. 2002; 99:3830-5; Yin X, et al. Oncogene 2003; 22:6151-9; Mo H, et al. Proc Natl Acad Sci USA 2006; 103:6344-9; Giorello L, Clerico L, Pescarolo M P, Vikhanskaya F, Salmona M, Colella G, et al. Inhibition of cancer cell growth and c-Myc transcriptional activity by a c-Myc helix 1-type peptide fused to an internalization sequence. Cancer Res 1998; 58:3654-9 and Jung K C, Park C H, Hwang Y H, Rhee H S, Lee J H, Kim H K, et al. Fatty acids, inhibitors for the DNA binding of c-Myc/Max dimer, suppress proliferation and induce apoptosis of differentiated HL-60 human leukemia cell. Leukemia 2006; 20; 122-7). A shortcoming of all low molecular weight compounds described thus far, however, has been their generally low potency, which detracts from their utility in actual clinical settings. This likely reflects their having been identified in screens of chemical libraries, whose finite contents are unlikely to contain clinically optimized structures (Lipinski C, Hopkins A. Navigating chemical space for biology and medicine. Nature 2004; 432:855-61). Thus, in the current study, we have attempted to rectify this by concentrating upon the least structurally complex member of our original set of index compounds, namely 10058-F4. The intention was to synthesize, or identify by in silico screens, 10058-F4-related "second generation" compounds with enhanced potency. These initial surveys were performed in three stages. In the first, the five-member rhodanine ring of 10058-F4 was maintained while modifying the six-member ring. In the second stage, modifications of only the rhodanine ring were evaluated. Together, this population of novel compounds provided a working library of analogs, a number of which proved superior to 10058-F4. Finally, we asked whether the best of these second generation structures could be combined to generate even more potent "third generation" compounds.

Realizing that the apparent efficacy of a compound might be influenced in either direction by the nature of the assay used in its evaluation, four different, and largely independent, assay systems were employed. These consisted of mammalian cell-based proliferation assays, a co-IP assay of c-Myc-Max complexes from nuclear extracts, an EMSA assay with highly purified c-Myc and Max proteins, and a simple, two-component fluorescence polarization assay to directly measure compound binding to the c-Myc bHLH-LZ domain. A large number of compounds structurally related to 10058-F4 demonstrated significant activities in each of these assays.

The utilization of multiple assays, while affirming the selectivity of certain analogs, nonetheless complicated their prioritization with regard to their in vivo efficacies. For example, several six-member ring-substituted analogs appeared superior to 10058-F4 in EMSA or co-IP assays but showed no better potency than 10058-F4 in HL60 cells. Examples of such compounds included 27RH and 28RH. Conversely, certain 5-member rhodanine ring-substituted compounds, such as #015 and #764, which demonstrated a significantly improved anti-proliferative effect against HL60 cells, did not necessarily prove superior to 10058-F4 in co-IP or EMSA assays. Although evaluation of the in vivo fates of these analogs is beyond the scope of the current work, these disparities among different assays likely reflect uncontrolled variables of cell-based assays such as compound uptake, stability, active efflux, and metabolism to more or less active analogs.

With regard to fluorescence polarization measurements (FIGS. 5 and 6), binding for all compounds generally occurred at concentrations lower than those needed to disrupt the c-Myc-Max interaction in other assays (kDs 0.5-8.6 µM: FIG. 6D). This likely reflects the fact that binding to monomeric c-Myc in solution occurs under conditions in which the bHLH-LZ domain exists in a mobile conformation of only partial, or transitory, α-helical content (Fieber W, Schneider M L, Matt T, Krautler B, Konrat R, Bister K. Structure, function, and dynamics of the dimerization and DNA-binding domain of oncogenic transcription factor v-Myc. J Mol Biol 2001; 30:1395-410). Other assays, all of which involve the presence of Max, involve a competition between Max and the compound and are thus influenced by differences in the free energy of c-Myc-Max heterodimer formation. For example, EMSAs were performed under conditions in which complete or nearly complete binding of the protein heterodimer to the E-box-containing oligonucleotide occurs in the absence of inhibitor. The disruption of such a protein-DNA complex at the top of its titration curve is energetically more difficult than is the disruption of the same complex under conditions of only partial binding (e.g. at or near the bottom of its titration curve). It is noted that some compounds (e.g. 28RH and 12RH-NCN-1), were quite effective at eliminating E-box binding by c-Myc-Max (FIGS. 4B-4D). Because the disruption observed in EMSAs is a function both of a compound's effectiveness and of the heterodimer's affinity at a particular concentration and set of binding conditions, comparison between compounds within a series is useful. However, results cannot be compared directly with those obtained under dissimilar conditions (Fieber W, et al. J Mol Biol 2001; 30:1395-410 and Kiessling A, Sperl B, Hollis A, Eick D, Berg T. Selective inhibition of c-Myc/Max dimerization and DNA binding by small molecules. Chem Biol 2006; 13:745-51).

An unexpected outcome of this study was that the activities of the best second generation compounds, such as 27RH, were not substantially improved when they were combined with the optimized rhodanine ring derivative to create "third generation" compounds (FIG. 3 and data not shown). This may reflect the nature of binding to an intrinsically disordered protein where a single "best fit" between the compound and the target may, in fact, not exist. Thus, the protein conformation that optimizes contacts with the rhodanine ring and the substituted phenyl ring may be quite different from that which optimizes contacts with the rhodanine ring and the piperidine ring in the case of RH-NCN1 (FIG. 3B). Binding a particular protein conformation produces an entropic penalty either from organization of certain residues into a binding conformation or from selecting one particular structure out of the ensemble of possible conformations. The current compounds may not be able to organize (or capture) a sufficiently large region of the peptide in an energetically favorably way such that the binding gains from substitutions at either end of the molecule are cumulative.

Because the number of third generation compounds was by necessity limited, we are unable to state with any certainty that their relatively poor potencies constitute a general property. However, these findings do suggest that future improvements in compound efficacy are more likely to accrue from considerations based upon the actual 3-dimensional structure of the c-Myc bHLH-LZ in association with a compound obtained by techniques such as NMR spectroscopy or x-ray crystallography. At a minimum, determining these structures is likely to provide help in determining which chemical groups on the low molecular weight moieties that can be modified so as to maximize and/or stabilize their interaction with the peptide. Despite the above caveats, it is seen that simple alterations of an index compound, such as 10058-F4, can lead to significant improvements in efficacy. This provides reason to believe that additional modifications of the structures presented here might continue to provide a source of novel compounds with improved efficacies. Their utility may perhaps be optimized even further when combined with other, unrelated low molecular weight agents that independently target other regions of the c-Myc bHLH-LZ domain.

We claim:

1. A compound having the structure (Formula I):

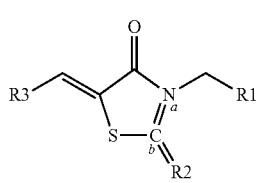

wherein R1 is a 5-6 atom heterocyclic group;
R2 is O, S, $C_{1-3}$ alkoxyl group, or $C_{1-3}$ alkylthiyl group; and
R3 is one of phenyl, a substituted phenyl, cylcohexyl, and substituted cyclohexyl,
wherein the substituted phenyl comprises one or more of: a 2-, 3-, 4-, or 5-halide; a 3-, 4-, or 5-nitro group; a 3-, 4-, or 5-cyano group; a 3-, 4-, or 5-acyl group; a 3-, 4-, or 5-carboxyl group; a 3-, 4-, or 5-hydroxyl group; a 3-, 4-, 5- $C_{1-3}$ alkoxyl group; a $C_{1-4}$ saturated or unsaturated alkyl group;
and wherein the substituted cyclohexyl comprises one of: a 3-, 4-, or 5-halide; a 3-, 4-, 5-$C_{1-3}$ alkoxyl group; and a $C_{1-4}$ saturated or unsaturated alkyl group and a and/or b are single or double bonds, or a pharmaceutically acceptable salt thereof.

2. The compound of claim 1, wherein R2 is a $C_{1-3}$ alkoxyl group.

3. The compound of claim 2, wherein the $C_{1-3}$ alkoxyl group is a methoxyl group.

4. The compound of claim 1, wherein R2 is a $C_{1-3}$ alkylthiyl group.

5. The compound of claim 4, wherein the $C_{1-3}$ alkylthiyl group is a methylthiyl group.

6. The compound of claim 1, wherein R1 is one of

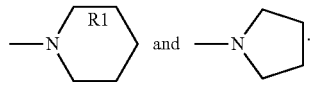

7. The compound of claim 1, having the structure

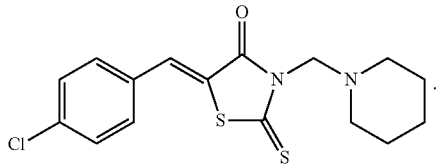

or a pharmaceutically acceptable salt thereof.

8. The compound of claim 1, having the structure:

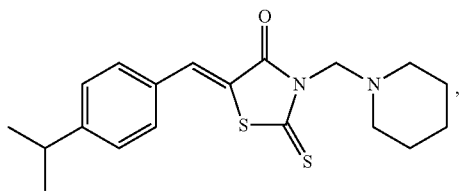

28 RH-NCN-1 or a pharmaceutically acceptable salt thereof.

9. The compound of claim 1, wherein the compound is a salt of one of an inorganic acid salt, an organic acid salt and a basic salt.

10. The compound of claim 1, wherein the compound is salt chosen from hydrochloric acid salts, hydrobromic acid salts, phosphoric acid salts, metaphosphoric acid salts, nitric acid salts, sulfuric acid salts, acetic acid salts, benzenesulfonic acid salts, benzoic acid salts, citric acid salts, ethanesulfonic acid salts, fumaric acid salts, gluconic acid salts, glycolic acid salts, isethionic acid salts, lactic acid salts, lactobionic acid salts, maleic acid salts, malic acid salts, methanesulfonic acid salts, succinic acid salts, p-toluenesulfonic acid salts, tartaric acid salts, ammonium salts salts, alkali metal salts, alkaline earth metal salts, trometamol (2-amino-2-hydroxymethyl 1,3-propanediol) salts, diethanolamine salts, lysine salts or ethylenediamineone salts.

11. The compound of claim 1, having the structure:

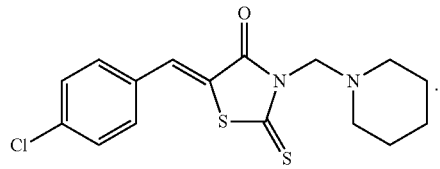

12. The compound of claim 1, having the structure:

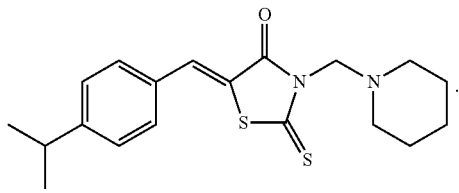

28 RH-NCN-1

* * * * *

UNITED STATES PATENT AND TRADEMARK OFFICE
CERTIFICATE OF CORRECTION

PATENT NO. : 7,872,027 B2
APPLICATION NO. : 11/707421
DATED : January 18, 2011
INVENTOR(S) : Steven J. Metallo et al.

It is certified that error appears in the above-identified patent and that said Letters Patent is hereby corrected as shown below:

On the Title Page, Item 56:

Other Publications "andreflect" should be --and reflect--.

Other Publications "Karlssson" should be --Karlsson--.

Other Publications "Hetercycl" should be --Heterocycl--.

Other Publications "and and in mice" should be --and in mice--.

In the Specification:

Column 2, line 27 "Gree3nberg" should be --Greenberg--.

Column 3, line 43 "heterocyclicgroup" should be --heterocyclic group--.

Column 3, line 46 "cylcohexyl" should be --cyclohexyl--.

Column 5, line 5 " 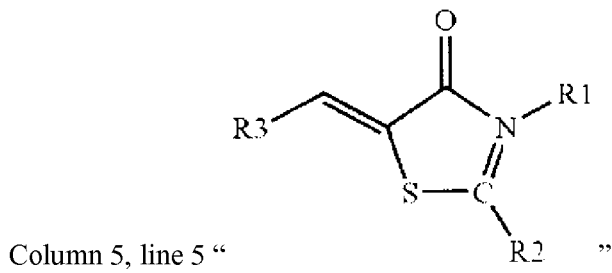 "

should be -- 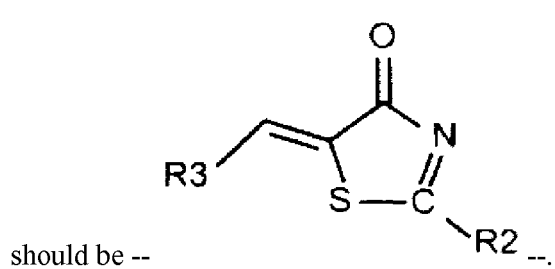 --.

Column 5, line 15 "cylcohexyl" should be --cyclohexyl--.

Column 5, line 37 "heterocyclicgroup" should be --heterocyclic group--.

Signed and Sealed this
Twenty-fifth Day of August, 2015

Michelle K. Lee
*Director of the United States Patent and Trademark Office*

CERTIFICATE OF CORRECTION (continued)

U.S. Pat. No. 7,872,027 B2

Column 5, line 39 "cylcohexyl" should be --cyclohexyl--.

Column 5, line 63 "cylcohexyl" should be --cyclohexyl--.

Column 6, line 59 "ammonium salts salts" should be --ammonium salts--.

Column 7, line 12 "heterocyclicgroup" should be --heterocyclic group--.

Column 7, line 16 "cylcohexyl" should be --cyclohexyl--.

Column 7, lines 38-39 "R1 is one of R1 is one of one of" should be --R1 is one of:--.

Column 7, line 56 "$O]_n$," should be --$O]_n$-,--.

Column 8, line 41 "cylcohexyl" should be --cyclohexyl--.

Column 10, line 20 "cell" should be --cells--.

Column 10, line 24 "198813:319-37" should be --1988; 13:319-37--.

Column 11, line 47 "waxe(s)" should be --wax(es)--.

Column 12, line 1 "prevent, reduce" should be --prevent and/or reduce--.

Column 12, line 63 "heterocyclicgroup" should be --heterocyclic group--.

Column 13, line 4 "cylcohexyl" should be --cyclohexyl--.

Column 13, line 21 "include chosen from one of" should be --include those chosen from one of--.

Column 13, line 40 "heterocyclicgroup" should be --heterocyclic group--.

Column 13, line 55 "cylcohexyl" should be --cyclohexyl--.

Column 14, line 2 "include chosen from one of" should be --include those chosen from one of--.

Column 14, line 27 "cylcohexyl" should be --cyclohexyl--.

Column 14, line 55 "thereof," should be --thereof;--.

Column 15, line 46 "hit21ead" should be --hit2lead--.

Column 16, lines 3-4 "74-9) Preparation" should be --74-9). Preparation--.

Column 16, line 6 "CH3I" should be --$CH_3I$--.

Column 16, line 28 "than" should be --then--.

Column 17, line 6 "4o C" should be --40°C--.

Column 18, line 57 "S–H" should be --S-H--.

Column 18, line 67 "27RH was" should be --27RH, was--.

Column 19, line 2 "28RH was" should be --28RH, was--.

Column 21, line 10 "lead" should be --leads--.

Column 21, line 10 "decreases" should be --decrease--.

Column 23, line 28 "v-Myc" should be --c-Myc--.

Column 24, line 36 "moieties that can" should be --moieties can--.

CERTIFICATE OF CORRECTION (continued)

In the Claims:

Column 25, line 5 " 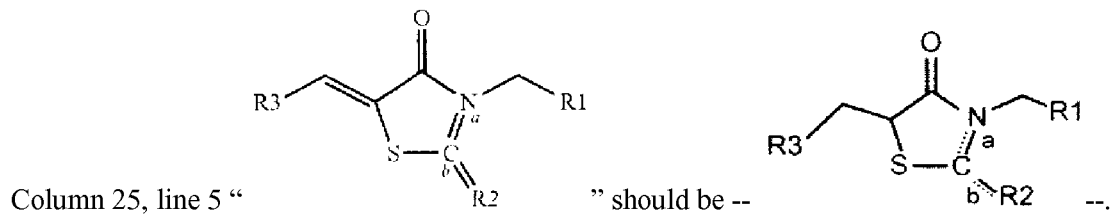 " should be -- --.

Column 25, line 15 "a substituted" should be --substituted--.

Column 25, line 15 "cylcohexyl" should be --cyclohexyl--.

Column 25, line 40 " 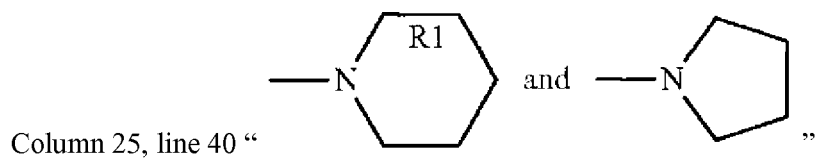 "

should be -- 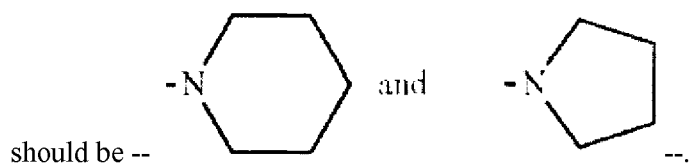 --.

Column 26, line 27 "ammonium salts salts" should be --ammonium salts--.

Column 26, line 29 "...methyl 1,3-..." should be --...methyl-1,3-...--.

SEQUENCE LISTING

<160> NUMBER OF SEQ ID NOS: 1

<210> SEQ ID NO 1
<211> LENGTH: 22
<212> TYPE: DNA
<213> ORGANISM: Artificial
<220> FEATURE:
<223> OTHER INFORMATION: synthesized DNA oligonucleotide

<400> SEQUENCE: 1
cacccggtca cgtggcctac ac                                          22